US012605455B2

(12) United States Patent
Mann

(10) Patent No.: US 12,605,455 B2
(45) Date of Patent: Apr. 21, 2026

(54) CAR PEPTIDE FOR IMPROVED CORONAVIRUS SURVIVAL

(71) Applicant: Vascular Biosciences, San Diego, CA (US)

(72) Inventor: David Mann, San Diego, CA (US)

(73) Assignee: Vascular Biosciences, San Diego, CA (US)

( * ) Notice: Subject to any disclaimer, the term of this patent is extended or adjusted under 35 U.S.C. 154(b) by 757 days.

(21) Appl. No.: 17/912,312

(22) PCT Filed: Mar. 19, 2021

(86) PCT No.: PCT/US2021/023333
§ 371 (c)(1),
(2) Date: Sep. 16, 2022

(87) PCT Pub. No.: WO2021/189004
PCT Pub. Date: Sep. 23, 2021

(65) Prior Publication Data
US 2023/0137434 A1     May 4, 2023

Related U.S. Application Data

(60) Provisional application No. 62/991,796, filed on Mar. 19, 2020.

(51) Int. Cl.
| | |
|---|---|
| A61K 47/55 | (2017.01) |
| A61K 9/00 | (2006.01) |
| A61K 9/127 | (2006.01) |
| A61K 31/197 | (2006.01) |
| A61K 31/573 | (2006.01) |
| A61K 31/706 | (2006.01) |
| A61K 38/08 | (2019.01) |
| A61K 38/21 | (2006.01) |
| A61K 38/36 | (2006.01) |
| A61K 39/395 | (2006.01) |
| A61K 47/64 | (2017.01) |
| A61K 49/10 | (2006.01) |
| A61K 49/14 | (2006.01) |
| A61K 49/18 | (2006.01) |
| A61K 51/08 | (2006.01) |
| A61P 3/10 | (2006.01) |
| A61P 9/00 | (2006.01) |
| A61P 29/00 | (2006.01) |
| A61P 31/14 | (2006.01) |
| A61P 37/06 | (2006.01) |

(52) U.S. Cl.
CPC ............ *A61K 47/646* (2017.08); *A61K 9/007* (2013.01); *A61K 9/127* (2013.01); *A61K 31/197* (2013.01); *A61K 31/573* (2013.01); *A61K 31/706* (2013.01); *A61K 38/08* (2013.01); *A61K 38/21* (2013.01); *A61K 38/36* (2013.01); *A61K 39/3955* (2013.01); *A61K 47/55* (2017.08); *A61K 49/106* (2013.01); *A61K 49/14* (2013.01); *A61K 49/1866* (2013.01); *A61K 51/088* (2013.01); *A61P 3/10* (2018.01); *A61P 9/00* (2018.01); *A61P 29/00* (2018.01); *A61P 31/14* (2018.01); *A61P 37/06* (2018.01)

(58) Field of Classification Search
None
See application file for complete search history.

(56) References Cited

U.S. PATENT DOCUMENTS

| | | | |
|---|---|---|---|
| 9,180,161 B2 | 11/2015 | Komatsu et al. | |
| 9,629,877 B2 | 4/2017 | Cooper et al. | |
| 2015/0183854 A1 | 7/2015 | Mori et al. | |
| 2019/0022170 A1* | 1/2019 | Mann ..................... | G16C 20/60 |
| 2020/0289573 A1 | 9/2020 | Li et al. | |

FOREIGN PATENT DOCUMENTS

| | | |
|---|---|---|
| WO | 20040029093 | 4/2004 |
| WO | 20110106788 | 9/2011 |
| WO | 20130134781 | 9/2013 |
| WO | 20160022610 | 2/2016 |
| WO | 20180213928 | 11/2018 |

OTHER PUBLICATIONS

Agostini et al., "Coronavirus Susceptibility to the Antiviral Remdesivir (GS-5734) Is Mediated by the Viral Polymerase and the Proofreading Exoribonuclease," mBio, Mar. 6, 2018, vol. 9, Iss. 2, p. 1-15.
Koss et al., "Sanofi and Regeneron begin global Kevzara (sarilumab) clinical trial program in patients with severe COVID-19," Sanofi Press Releases, Mar. 16, 2020, p. 1-6.
Yehya et al., "Improved Survival After Surgical Sepsis in Rats Using a Novel Vascular Homing Peptide to Target Endothelial Delivery of Hydrocortisone," American Journal of Respiratory and Critical Care Medicine, May 1, 2020, vol. 201, p. A2595-A2595.

* cited by examiner

*Primary Examiner* — Celeste A Roney
(74) *Attorney, Agent, or Firm* — Lewis Kohn & Walker LLP; David M. Kohn; Kari Moyer-Henry

(57)     ABSTRACT

A conjugate for treating an individual suffering from a disease, wherein the conjugate is comprised of: a targeting peptide comprising a sequence substantially identical to CAR, or a variant thereof; and at least one therapeutic molecule and methods for making and administering same. Also disclosed is a combination product for use in the treatment of a disease, wherein the combination product comprises: (a) a targeting peptide comprising a sequence substantially identical to CAR, or a variant thereof; (b) a liposome, wherein the targeting peptide is encapsulated within the liposome; and (c) an effective amount of an anti-inflammatory agent and methods for making and administering same.

5 Claims, 32 Drawing Sheets

CAR + Dexamethasone in a COVID19 Animal Model

Group 1: Placebo (PBS)
Group 2: 0.15 mg/kg Dexamethasone
Group 3: 0.15 mg/kg Dexamethasone + 8 mg/kg CAR

CAR + Methylprednisolone in a COVID-19 Animal Model

K18-hACE2 Male Transgenic
Mice (Jackson Lab #034860)

Group 1: Placebo (PBS)
Group 2: 2 mg/kg  Methylprednisolone  (MPS) ip
Group 3:  2 mg/kg  Methylprednisolone  + 8 mg/kg CAR ip (CAR +
MPS)

CAR + Hydrocortisone in a COVID-19 Animal Model

K18-hACE2 Male Transgenic
Mice (Jackson Lab #034860)

Group 1: Placebo (PBS)
Group 2: 0.2 mg/kg HCT  ip (HCT)
Group 3: 0.2  mg/kg HCT + 8 mg/kg CAR (CAR + HCT)

CAR + Dexamethasone Phase II COVID19 Clinical Trial

Group 1: Placebo (PBS)
Group 2: 6 mg/dose/day Dexamethasone iv ( Dex)
Group 3: 6 mg /dose/day  Dexamethasone + 3 mg/kg CAR iv (CAR + Dex)

CAR + Low DoseDexamethasone PhaseII COVID-19 Clinical Trial

Group 1: Placebo (PBS)
Group 2: 6 mg/dose/day Dexamethasone iv ( Dex)
Group 3: 1 mg/dose/day Low Dose Dexamethasone + 3 mg/kg CAR iv
            (CAR + Low Dose Dex)

CAR + Methylprednisolone Phase II COVID-19 Clinical Trial

Group 1: Placebo (PBS)
Group 2: 16 mg/dose x twice daily 32 mg/day Methylprednisolone iv (MPS)
Group 3:  16 mg/dose x twice daily 32 mg/day   Methylprednisolone
        + 3 mg/kg CAR iv (CAR + MPS)

CAR + Low Dose Methylprednisolone Phase II COVID19 Clinical Trial

Hospitalized
COVID -19 Patients
On Supplemental O₂

Group 1: Placebo (PBS)
Group 2: 16 mg/dose x twice daily = 32 mg/day Methylprednisolone iv (MPS)
Group 3: 2 mg/dose x twice daily = 4 mg/day Methylprednisolone
        + 3 mg/kg CAR iv (CAR + MPS)

CAR + Hydrocortisone Phase II COVID19 Clinical Trial

Hospitalized
COVID -19 Patients
On Supplemental O$_2$

Group 1: Placebo (PBS)
Group 2: 40 mg/dose 4x daily = 160 mg/day Hydrocortisone iv (HCT)
Group 3:  40 mg/dose 4x daily = 160 mg/day Hydrocortisone   iv
       + 3 mg/kg CAR iv (CAR + HCT)

CAR + Low Dose HydrocortisonePhase II COVID19 Clinical Trial

Group 1: Placebo (PBS)
Group 2: 40 mg/dose 4x daily = 160 mg/day Hydrocortisone iv (HCT)
Group 3: 8  mg/dose 4x daily =  32 mg/day Hydrocortisone  + 3 mg/kg CAR iv
            (CAR + Low Dose HCT)

Group 1: Placebo (PBS)
Group 2: 25 mg/kg/dose x 2 daily every 12 hours    Remdesivir ip (RDV)
Group 3: 25 mg/kg/dose x 2 daily every 12 hours    Remdesivir
         + 8 mg/kg CAR ip (CAR + RDV)

CAR + RemdesivirPhase II COVID-19 Clinical Trial

Hospitalized
COVID-19 Patients
On Supplemental O₂

Group 1: Placebo (PBS)
Group 1: Placebo (PBS)
Group 2: one injection of Remdesivir 200 mg day 1, 100 mg/day days 2-10,
        infused over 30 – 120 min iv (RDV)
Group 3: one injection of Remdesivir 200 mg day 1, 100 mg/day days 2-10,
        infused over 30 – 120 min iv + 3 mg/kg CAR iv (CAR + RDV)

Group 1: Placebo (PBS)
Group 2: Antithrombin III 300 IU/kg/dose ip every 24 hours (ATIII)
Group 3: Antithrombin III 300 IU/kg/ dose + 8 mg/kg CAR ip
every 24 hours (CAR + ATIII)

CAR + Agatroban     Phase II COVID-19 Clinical Trial

Group 1: Placebo (PBS)
Group 2: Agatroban 0.7 mg/kg/day infused at a rate of 1 ug/kg/min for a total dose
of 50 mg for a 71.4 kg human iv (Aga)
Group 3: Agatroban 0.7 mg/kg/day infused at a rate of 1 ug/kg/min for a total dose
of 50 mg for a 71.4 kg human + CAR 3 mg/kg co-infusion at a rate of 5 ug/kg/min.
(CAR + Aga)

SARS-  CAR + Remdesivir + Dexamethasone in a COVID-19 Animal Model
CoV2

K18-hACE2 Male Transgenic
Mice (Jackson Lab #034860)

Group 1: Placebo (PBS)
Group 2: 25 mg/kg Remdesivir + 0.15 mg/kg Dexamethasone
        (RDV + DEX) ip
Group 3: 25 mg/kg Remdesivir + 0.15 mg/kg Dexamethasone
+ 8 mg/kg CAR (CAR + RDV +DEX) ip

CAR + Interferon in a COVID-19 Animal Model

Group 1: Placebo (PBS)
Group 2: 2 µg interferon
Group 3: 2 µg interferon + 3 mg/kg CAR

CAR-nps for MRI Imaging of COVID-inflamed Tissues

K18-hACE2 Male Transgenic Mice (Jackson Lab #034860)
+ SARs CoV2 2.3 x 10⁴ pfu

Group 1 → GAD 0.1 mmol/kg

Group 2 → CAR-$Fe_2O_3$ 0.1 mmol/kg

⟶ Extent of Imaging

CAR-nps for MRI Imaging of COVID-inflamed Tissues

K18-hACE2 Male Transgenic Mice (Jackson Lab #034866)
+ SARs CoV2 2.3 x 10⁴ pfu

Group 1          Group 2                    → Extent of Imaging

GDP 0.1mmol/kg     CAR-Fe₂O₃
                   0.1 mmol/kg

CAR-Au for CT Scan of COVID-inflamed Tissues

CAR-Liposomes + Dexamethasone in a COVID19 Animal Model

Group 1: Placebo (Saline)
Group 2: 0.15 mg/kg Dexamethasone
Group 3: 0.15 mg/kg liposome encapsulated Dexamethasone
Group 4: 0.15 mg/kg CAR-liposome encapsulated Dexamethasone

CAR-Liposomes + Methylprednisolone in a COVID-19 Animal Model

Group 1: Placebo (Saline)
Group 2: 2 mg/kg MPS
Group 3: 2 mg/kg liposome encapsulated MPS
Group 4: 2 mg/kg CAR -liposome encapsulated MPS Group 1: Placebo (Saline)
Group 2: 0.2 mg/kg HCT
Group 3: 0.2 mg/kg liposome encapsulated HCT
Group 4: 0.2 mg/kg CAR -liposome encapsulated HCT Group 1: Placebo (Saline)
Group 2: 0.15 mg/kg Dexamethasone
Group 3: 0.15 mg/kg liposome encapsulated Dexamethasone
Group 4: 0.15 mg/kg CAR-liposome encapsulated Dexamethasone

CAR-Liposomes + Methyprednisolonein a COVID-19 Animal Model

Group 1: Placebo (Saline)
Group 2: 2 mg/kg MPS
Group 3: 2 mg/ kg liposome encapsulated MPS
Group 4: 2 mg/kg CAR -liposome encapsulated MPS

CAR-Liposomes + Hydrocortisone in a COVID-19 Animal Model

K18-hACE2 Male Transgenic Mice (Jackson Lab #034860)

Group 1: Placebo (Saline)
Group 2: 0.2 mg/kg HCT
Group 3: 0.2 mg/kg liposome encapsulated HCT
Group 4: 0.2 mg/kg CAR-liposome encapsulated HCT

CAR PEPTIDE FOR IMPROVED CORONAVIRUS SURVIVAL

RELATED APPLICATIONS

This application is a U.S. National Phase application under 35 U.S.C. § 371 from International Patent Application No. PCT/US2021/023333 filed Mar. 19, 2021, which claims the benefit of priority from U.S. Provisional Application No. 62/991,796 filed Mar. 19, 2020.

FIELD OF THE INVENTION

This application relates generally to the field of homing peptides in the use of treating and/or preventing specific diseases. Specifically, this application relates to treatments for coronavirus infections in order to improve patient survival based on novel therapeutic combinations.

BACKGROUND OF THE INVENTION

The COVID-19 infection causes a severe respiratory illness similar to severe acute respiratory syndrome coronavirus (SARS-COV or SARS-CoV2), with such infection being associated with significant mortality for those contracting the disease.

As of Mar. 17, 2021, there have been 121,772,806 in worldwide confirmed cases of COVID-19 and 2,691,024 deaths caused by the virus (https://www.worldometers.info/coronavirus/, accessed on Mar. 17, 2021).

In the publication "Clinical features of patients infected with the 2019 novel coronavirus in Wuhan, China" Huang, et. al looked at the clinical differences between COVID-19 patients that required ICU admission and those that did not. It was noted that the patients that were admitted to the ICU had much higher levels of inflammatory cytokines than those who were not.

This increase in cytokines, or "cytokine storm", can lead to viral sepsis in these patients. In turn, this viral sepsis can lead to pneumonitis, acute respiratory distress syndrome (ARDS), multi-organ failure, secondary bacterial pneumonia, and death. Sepsis is a medical emergency involving life-threatening organ dysfunction due to a mis-regulated response to infection. Despite decades of research, novel therapies to facilitate precision medicine for sepsis beyond resuscitation and infectious source control remain elusive.

The systemic immuno-inflammatory response associated with sepsis causes endothelial injury not only at the site of infection but across vital organ systems. Damage to the endothelium results in glycocalyx shedding, breakdown of tight junctions with capillary leak, and a pro-coagulant microvasculature that contributes to progressive or persistent multiple organ dysfunction syndrome (MODS) and, without remedy, eventual death (Okada H, Yoshida S, Hara A, Ogura S, Tomita H. Vascular endothelial injury exacerbates coronavirus disease 2019: The role of endothelial glycocalyx protection [published online ahead of print, 2020 Aug. 13]. *Microcirculation*. 2020; e 12654).

In 2015, an international group of sepsis experts called for novel therapeutics that target the injured vascular endothelium and restore endothelial homeostasis in sepsis (Ince C, Mayeux P R, Nguyen T, et al. THE ENDOTHELIUM IN SEPSIS. *Shock*. 2016; 45(3):259-270). Corticosteroids, such as hydrocortisone (HCT), have been investigated for treating sepsis, largely through attenuation of the systemic inflammatory effects on the vascular endothelium.

Corticosteroids were used frequently for treatment of patients with severe illness after infection of COVID-19 for possible benefit by reducing inflammatory-induced lung injury. However, current evidence from treatment of other types of coronaviruses (SARS-CoV and MERS-CoV) suggests that receiving corticosteroids did not have an effect on mortality.

A key challenge is the substantial heterogeneity in patient response to HCT, which appears driven, in part, by variability in gluococorticoid receptor expression and sensitivity. In addition, corticosteroids are an imprecise therapy with off-target effects on immune suppression, myopathy, and hyperglycemia that expose patients to harm. Thus, despite biological plausibility and clinician enthusiasm for hydrocortisone, the ability to safely and effectively target this therapy remains a critical gap in knowledge (Annane D, et al. Guidelines for the diagnosis and management of critical illness-related corticosteroid insufficiency (CIRCI) in critically ill patients (Part I): Society of Critical Care Medicine (SCCM) and European Society of Intensive Care Medicine (ESICM) 2017. *Intensive Care Med*. 2017 December; 43(12):1751-1763).

While several agents targeting the dysfunctional endothelium have been tested in sepsis, none have demonstrated improvement in endothelial injury across multiple organ systems or increased survival (Cohen J, Vincent J L, Adhikari N, et al. Sepsis: a roadmap for future research. *Lancet Infect Dis* 2015; 15: 581-614). An ideal novel agent would exhibit selectivity for the endothelium of inflamed and injured tissues, concentrate therapeutic effects upon actively remodeling organs, arrest or even reverse the underlying process of sepsis-associated inflammation and endothelial damage, and minimize side effects and toxicities resulting in substantial improvements in mortality and morbidity.

Here we propose to transform low dose hydrocortisone into a precision therapy to improve survival of COVID-19 patients who develop sepsis through co-administration of low dose hydrocortisone with CARSKNKDC (CAR) peptide. CAR is a positively charged disulfide-linked cyclic peptide with high sequence homology to protein heparin-binding domains. It was originally identified through a phage display screen of peptides that shows enhanced binding to the vasculature of soft tissue wounds (Järvinen T A, Ruoslahti E. Molecular Changes in the Vasculature of Injured Tissues. *The American Journal of Pathology*. 2007; 171(2):702-711). Subsequently, CAR has also been shown to home to hypertensive pulmonary vessels, where it penetrates the damaged endothelium (Urakami T, et al. Peptide-Directed Highly Selective Targeting of Pulmonary Arterial Hypertension. *The American Journal of Pathology*. 2011; 178(6):2489-2495). Co-administration of CAR with three different classes of vasodilators doubled the pulmonary-specific vasodilation efficiency of these drugs in pre-clinical rat models of pulmonary hypertension (Toba M, et al. A Novel Vascular Homing Peptide Strategy to Selectively Enhance Pulmonary Drug Efficacy in Pulmonary Arterial Hypertension. *The American Journal of Pathology*. 2014; 184(2):369-375). Isolated perfused lung experiments indicate that CAR most likely achieved this effect by doubling the concentration of the co-administered drug in the diseased lung (Id.).

It was discovered that CAR selectively accumulates at sites of endothelial injury after exposure to lipopolysaccharide (LPS) and enhances the therapeutic effects of low-dose hydrocortisone to improve survival in LPS-induced endotoxemia. Specifically, it was demonstrated that the co-administration of CAR+hydrocortisone restored damaged endothelium to normal microscopic structure and increased survival in LPS-challenged mice to 90% compared to 30% for mice treated with low-dose hydrocortisone alone (P<0.05). It was also demonstrated that CAR has affinity for and accumulates within the endothelium, adventitia, and interstitium of the kidney, lung, and liver in mice with endotoxemia, but not in healthy tissues.

More recently, improved survival and lower endotheliopathy biomarkers (angiopoietin [ang]-2/ang-1 ratio) were demonstrated after cecal ligation and puncture (CLP) in rats treated with CAR+low dose hydrocortisone compared to saline or hydrocortisone alone. Importantly, CAR peptide worked via a co-administration effect without requiring direct conjugation to hydrocortisone.

It is proposed to utilize CAR peptide, which specifically targets and accumulates in diseased or damaged endothelium, as a novel adjuvant to more precisely and effectively target hydrocortisone in COVID-19 patients that have developed acute respiratory distress, multi-organ failure, sepsis, septic shock, and refractory septic shock and are at high risk for death. Our strong preliminary data that CAR+hydrocortisone augments the healing effects compared to hydrocortisone alone in endotoxemia, supplemented by additional data that CAR improves homing of multiple vasodilators to hypertensive pulmonary vessels in a model of pulmonary hypertension, support that CAR provides a novel and realistic approach to implement precision medicine for critically ill coronavirus patients. Because CAR peptide has demonstrated homing to multiple organs affected in endotoxemic models of sepsis, we further expect CAR peptide synergy when CAR peptide is co-administered with other coronavirus therapies in a similar manner to other drugs that CAR peptide has already enabled localized effects. CAR peptide having already demonstrated the ability to enhance fasudil, imatinib, sildenafil, treprostinil, macitentan, riociguat, hydrocortisone, sivelestat, and anti-thrombin IIII in animal models. It is further believed that CAR peptide could be utilized as an adjuvant for other Coronavirus therapies such as anti-viral therapies, to increase their localized activity and therefore the efficiency of co-administered coronavirus therapies.

The current approach to precision medicine requires a priori knowledge of a specific patient genotype or biomarker-based biological phenotype that may not be feasible to measure at the bedside, especially in a relevant timeframe for critically ill patients with COVID-19 that have developed sepsis. In contrast, CAR has the potential to enhance in vivo selectivity of low-dose hydrocortisone by targeting drug delivery and its beneficial effects to sites of endothelial injury without requiring additional a priori knowledge about the sites or severity of such damage.

SUMMARY OF THE INVENTION

The present invention provides for a method of treating an individual suffering from a disease, the method comprising: providing a targeting peptide comprising a sequence substantially identical to CAR, or a variant thereof; providing at least one therapeutic molecule which conveys a measurable therapeutic benefit to a disease selected from the group consisting of viral infection, sepsis, septic shock, acute respiratory distress syndrome, pneumonitis, and secondary bacterial pneumonia; co-administering a composition comprising a) and b) to an individual in need thereof; and measuring a therapeutic benefit to the individual. Preferably, the therapeutic molecule is a steroid. Preferably, the steroid is a corticosteroid. More preferably, the corticosteroid is at least one selected from the group consisting of dexamethasone, methylprednisolone and hydrocortisone. Alternatively, the therapeutic molecule is an antiviral drug.

In one aspect, the disease is a coronavirus. Preferably, the coronavirus disease is Covid-19 or a variant related thereto.

In an alternative embodiment, the present invention further provides for a conjugate for treating an individual suffering from a disease, wherein the conjugate is comprised of: a targeting peptide comprising a sequence substantially identical to CAR, or a variant thereof; and at least one therapeutic molecule. In one aspect, the therapeutic molecule is a corticosteroid selected from the group consisting of dexamethasone, methylprednisolone and hydrocortisone.

In another aspect, the disease is sepsis. In another aspect, the disease is a coronavirus. Preferably, the coronavirus disease is Covid-19 or a variant related thereto.

In another embodiment, the present invention provides for a combination product for use in the treatment of a disease, wherein the combination product comprises: (a) a targeting peptide comprising a sequence substantially identical to CAR, or a variant thereof; (b) a liposome, wherein the targeting peptide is encapsulated within the liposome; and (c) an effective amount of an anti-inflammatory agent. Preferably, the anti-inflammatory agent is a corticosteroid selected from the group consisting of dexamethasone, methylprednisolone and hydrocortisone. In another aspect, the combination product is administered in a dosing range of about 0.1 mg/kg/dose to about 4 mg/kg/dose, with administration being one selected from the group consisting of intravenous, inhalation and nasal.

In another aspect, the combination product further comprises at least one immune agent selected from the group consisting of antivirals, antibodies, IL-6 receptor antagonists, interferons and JAK inhibitors. Preferably, the at least one immune agent is remdesivir. Alternatively, the at least one immune agent is tocilizumab.

In yet another embodiment, the present invention provides for a method of determining a presence, extent and location of an injury comprising inflamed organs or tissues, the method comprising:

(a) providing a targeting peptide comprising a sequence substantially identical to CAR, or a variant thereof;

(b) providing an effective amount of a nanoparticle, wherein the nanoparticle comprises a contrast agent;

(c) combining the targeting peptide with the nanoparticle to form a combination agent; and (d) administering the combination agent to an individual suffering from the injury. Preferably, the nanoparticle is selected from the group consisting of $Fe_2O_3$ and Au.

In an alternative embodiment, the present invention provides for a conjugate for use in imaging inflamed tissues or organs of an individual, the conjugate comprising: (a) a targeting peptide comprising a sequence substantially identical to CAR, or a variant thereof; and (b) a chelating agent, wherein the conjugate is administered to the individual suffering an injury related to the inflamed tissues or organs. Preferably, the chelating agent is $^{64}$Cu-DOTA.

In yet another aspect, the disease is selected from the group consisting of viral infection, sepsis, septic shock, acute respiratory distress syndrome, pneumonitis, and secondary bacterial pneumonia. Preferably, the disease is a coronavirus. More preferably, the coronavirus disease is Covid-19 or a variant related thereto.

BRIEF DESCRIPTION OF THE DRAWINGS

The novel features of the present invention are set forth herein embodied in the form of the claims of the invention.

Features and advantages of the present invention may be best understood by reference to the following detailed description of the invention, setting forth illustrative embodiments and preferred features of the invention, as well as the accompanying drawings, of which.

Figure 23:
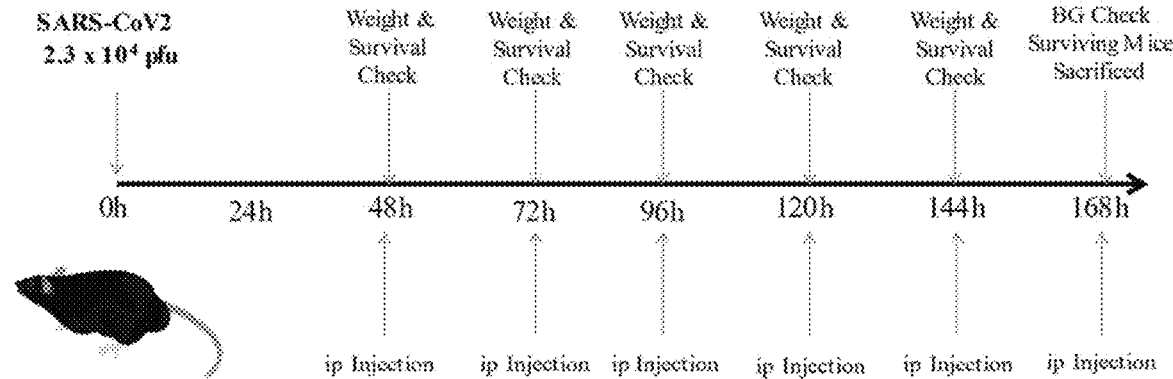

FIG. 23 shows a proof-of-concept experiment, using the K18-hACE2 transgenic mouse model, which has been modified to incorporate human angiotensin I-converting enzyme 2 (hACE2). 60 K18-hACE2 male transgenic mice are used, with administration of intranasal inoculations of SARS-CoV2 at $2.3 \times 10^4$ plaque-forming units to each mouse, then dividing them into 3 equal-sized treatment groups of 20 mice each: Group 1 (Placebo)—will receive placebo (PBS) injections ip every 12 hours; Group 2 (ATIII)—will receive antithrombin III 300IU/kg/dose ip every 24 hours; Group 3 (CAR+ATIII)—will receive antithrombin III 300IU/kg/dose ip every 24 hours co-administered with CAR peptide administered ip 8 mg/kg every 24 hours.

Figure 24:
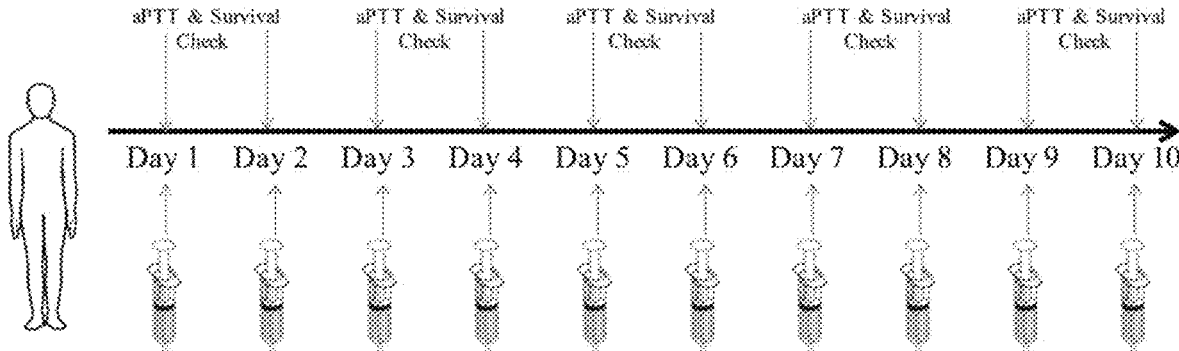

FIG. 24 shows a proposed study of agatroban in humans: 0.7 mg/kg/day infused at a rate of 1 ug/kg/min for a total dose of 50 mg for a 71.4 kg human. Activate partial thromboplastin time (aPTT) must be monitored to maintain a range of 30-40 seconds. If aPTT remains too high, administer supplemental doses of agrobatan, if aPTT is too low, reduce agratrabon dose. +/−CAR 3 mg/kg co-infusion at a rate of 5 ug/kg/min.

Figure 25:
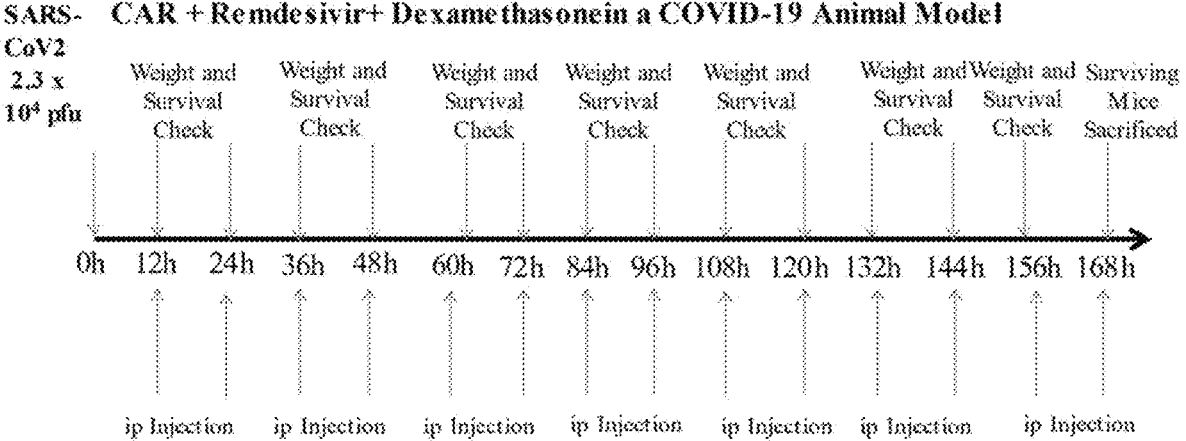
Figure 25:

FIG. 25 shows a proof-of-concept experiment, using the K18-hACE2 transgenic mouse model, which has been modified to incorporate human angiotensin I-converting enzyme 2 (hACE2). 60 K18-hACE2 male transgenic mice are used, with administration of intranasal inoculations of SARS-CoV2 at $2.3 \times 104$ plaque-forming units to each mouse, then dividing them into 3 equal-sized treatment groups of 20 mice each: Group 1 (Placebo)—will receive placebo (PBS) injections ip every 12 hours; Group 2 (RDV+Dex)—will receive remdesivir 25 mg/kg/dose ip every 12 hours and dexamethasone 0.15 mg/kg/dose ip every 24 hours; Group 3 (CAR+RDV+Dex)—will receive remdesivir 25 mg/kg/dose ip every 12 hours co-administered with CAR peptide administered ip 8 mg/kg every 12 hours and dexamethasone 0.15 mg/kg/dose ip every 24 hours.

Figure 26:
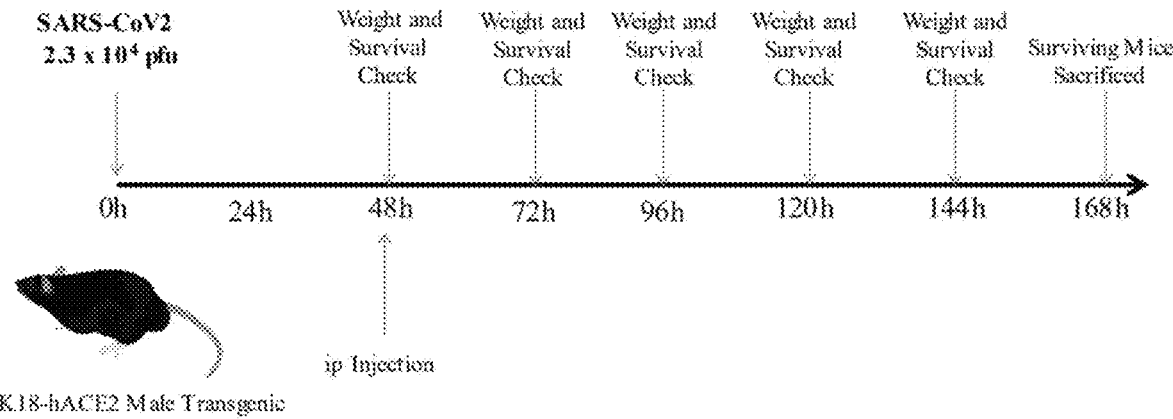

FIG. 26 shows a proof-of-concept experiment, using the K18-hACE2 transgenic mouse model, which has been modified to incorporate human angiotensin I-converting enzyme 2 (hACE2). 60 K18-hACE2 male transgenic mice are used, with administration of intranasal inoculations of SARS-CoV2 at $2.3 \times 10^4$ plaque-forming units to each mouse, then dividing them into 3 equal-sized treatment groups of 20 mice each: Group 1 (Placebo)—will receive placebo (PBS) injections i.p.; Group 2 (interferon)—will receive interferon (2 μg); Group 3 (CAR+interferon)—will receive interferon (2 μg) co-administered with CAR peptide (3 mg/kg).

Figure 27:

FIG. 27 shows a proof-of-concept experiment, using the K18-hACE2 transgenic mouse model, which has been modified to incorporate human angiotensin I-converting enzyme 2 (hACE2). 40 K18-hACE2 male transgenic mice are used, with administration of intranasal inoculations of SARS-CoV2 at $2.3 \times 10^4$ plaque-forming units to each mouse, then dividing them into 2 equal-sized treatment groups of 20 mice each: Group 1 (GAD) gadobutrol; Group 2 (CAR-Fe$_2$O$_3$NPs)—will receive CAR-Fe$_2$O$_3$NPs (CAR peptide—iron oxide nanoparticle contrast agent at a concentration of 100 μg/ml.

Figure 28:

FIG. 28 shows a proof-of-concept experiment, using the K18-hACE2 transgenic mouse model, which has been modified to incorporate human angiotensin I-converting enzyme 2 (hACE2). 40 K18-hACE2 male transgenic mice are used, with administration of intranasal inoculations of SARS-CoV2 at $2.3 \times 10^4$ plaque-forming units to each mouse, then dividing them into 2 equal-sized treatment groups of 20 mice each: Group 1 (GDP) gadopentetate dimeglumine; Group 2 (CAR-Fe$_2$O$_3$NPs)—will receive CAR-Fe$_2$O$_3$NPs (CAR peptide—iron oxide nanoparticle contrast agent at a concentration of 100 μg/ml.

Figure 29:
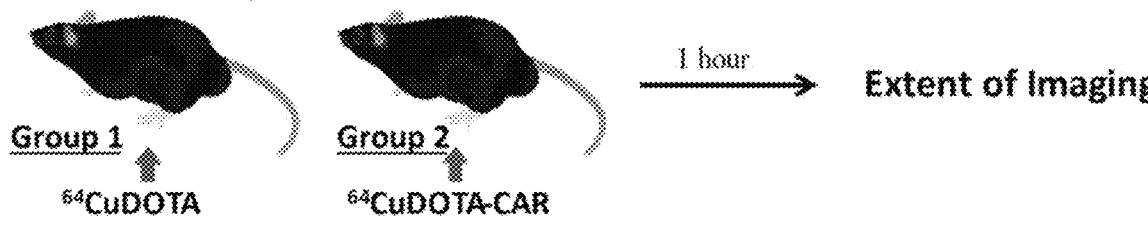

FIG. 29 shows an experiment to demonstrate the utility of CAR-chelate for PET/CT scanning of COVID-19-inflamed tissues in humans. 30 K18-hACE2 male transgenic mice (Jackson Lab #034860) would be used and administration of intranasal inoculations of SARS-CoV2 at $2.3 \times 10^4$ plaque-forming units would be delivered to each mouse. Once the mice have developed into an appropriate model for SARS-CoV-2, they would be divided into 2 groups of 15 SARS-CoV2-infected K18-hACE2 mice each: Group 1 ($^{64}$Cu-DOTA): SARSCoV2-infected K18-hACE2 mice will receive 100 μL of $^{64}$CuDOTA via the tail vein; Group 2 ($^{64}$Cu-DOTA-CAR): SARSCoV2-infected K18-hACE2 mice will receive 100 μL of $^{64}$Cu-DOTA-CAR via the tail vein.

Figure 30:
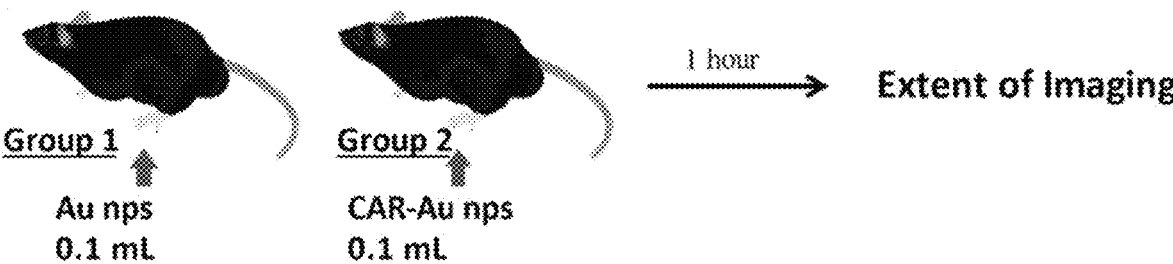

FIG. 30 shows an experiment to demonstrate the utility of CAR-Au for CT scanning of COVID-19-inflamed tissues in humans. 30 K18-hACE2 male transgenic mice (Jackson Lab #034860) would be used and administration of intranasal inoculations of SARS-CoV2 at $2.3 \times 10^4$ plaque-forming units would be delivered to each mouse. Once the mice have developed into an appropriate model for SARS-CoV-2, they would be divided into 2 groups of 15 SARSCoV2-infected K18-hACE2 mice each: Group 1 (Au nps): each mouse will receive an IV administration of 0.1 mL of 1.33 nM Au nps, $8 \times 1011$ nps/mL via tail vein; Group 2 (CAR-Au nps): each mouse will receive an IV administration of 0.1 mL of 1.33 nM CAR-Au nps, $8 \times 1011$ nps/mL via tail vein.

Figure 31:
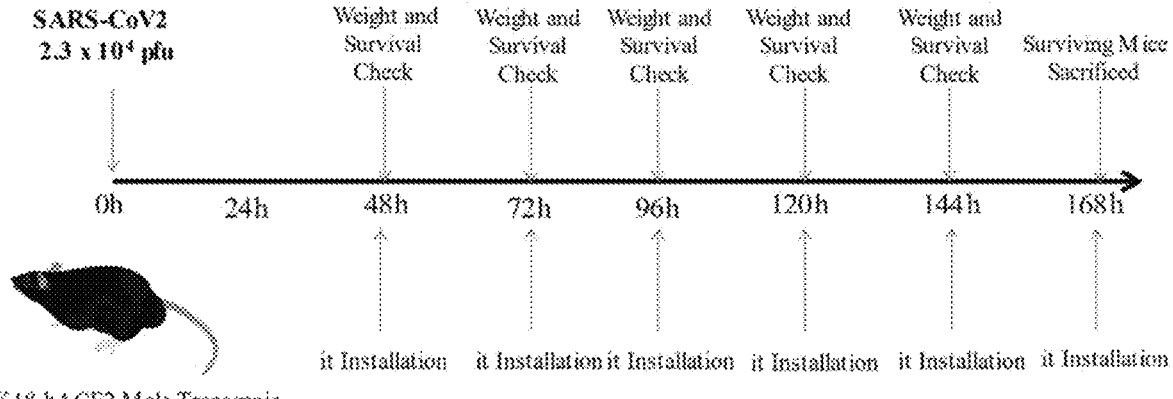

FIG. 31 shows an experiment to demonstrate the utility of CAR-liposomes peptide for treating COVID-19 disease in humans, using 80 K18-hACE2 male transgenic mice (Jackson Lab #034860) and administering intranasal inoculations of SARS-CoV2 at $2.3 \times 10^4$ plaque-forming units to each mouse. Once the mice have developed into an appropriate model for SARS-CoV-2, they are divided into 2 studies of equal size: pulmonary retention and survival. For the studies measuring survival against CAR-Liposomes with antivirals, 40 mice will be broken up into 4 groups equally: Group 1 (Placebo)—will receive PBS injected ip every 24 hours; Group 2 (Dex)—will receive dexamethasone 0.15 mg/kg/dose via IT installation every 24 hours; Group 3 (Dex Lip)—will receive liposome encapsulated dexamethasone 0.15 mg/kg/dose via IT installation every 24 hours; Group 4 (CAR-Lip+Dex)—will receive CAR-liposome encapsulated dexamethasone 0.15 mg/kg/dose IT every 24 hours.

Figure 32:
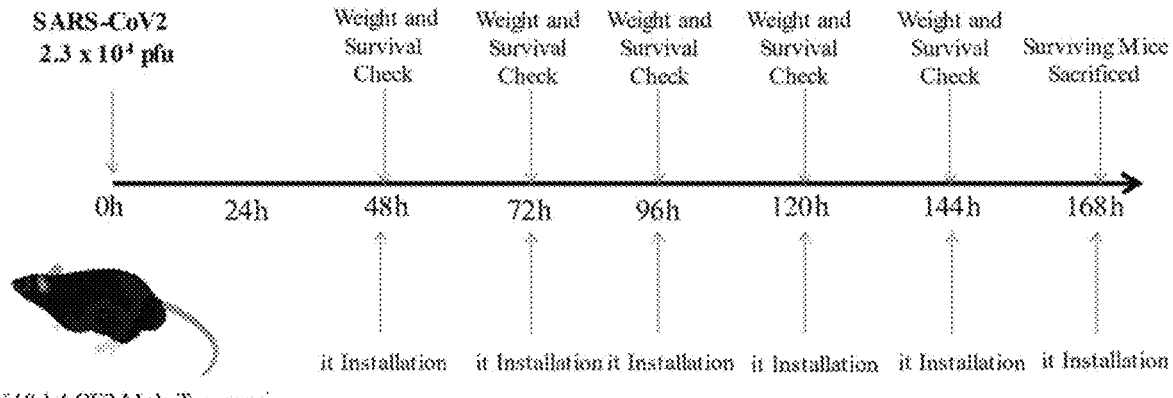

FIG. 32 shows an alternative formulation of CAR-liposome enhancement of methylprednisolone. To demonstrate CAR-liposome enhancement of methylprednisolone (MPS), SARS—Cov2 infected K18-hACE2 mice could receive methylprednisolone 2 mg/kg twice daily (every 12 hours). Liposomes will be formulated and validated as described in FIG. 31, with 4 groups divided as follows: Group 1 (Placebo)—will receive PBS injected ip every 24 hours; Group 2 (MPS)—will receive MPS 2 mg/kg/dose via IT installation every 24 hours; Group 3 (MPS Lip)—will receive liposome encapsulated MPS 2 mg/kg/dose via IT installation every 24 hours; Group 4 (CAR-Lip+MPS)—will receive Car-liposome encapsulated MPS 2 mg/kg/dose IT every 24 hours.

Figure 33:
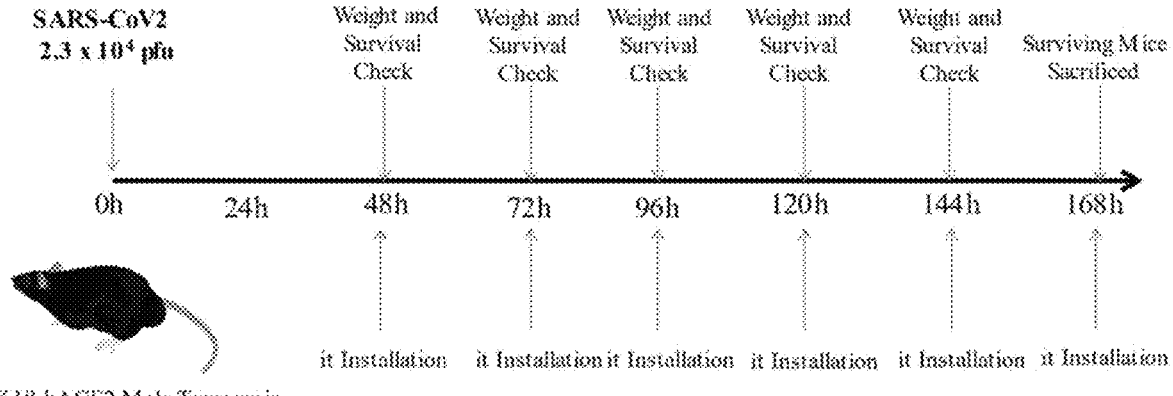

FIG. 33 shows an alternative formulation of CAR-liposome enhancement of hydrocortisone. To demonstrate CAR-liposome enhancement of hydrocortisone (HCT), SARS—Cov2 infected K18-hACE2 mice could receive hydrocortisone 0.2 mg/kg twice daily (every 12 hours). Liposomes will be formulated and validated as described in FIG. 31, with 4 groups divided as follows: Group 1 (Placebo)—will receive PBS injected ip every 24 hours; Group 2 (HCT)—will receive HCT 0.2 mg/kg/dose via IT installation every 24 hours; Group 3 (HCT Lip)—will receive liposome encapsulated HCT 0.2 mg/kg dose via IT installation every 24 hours; Group 4 (CAR-Lip+HCT)—will receive Car-liposome encapsulated HCT 0.2 mg/kg/dose IT every 24 hours.

Figure 34:
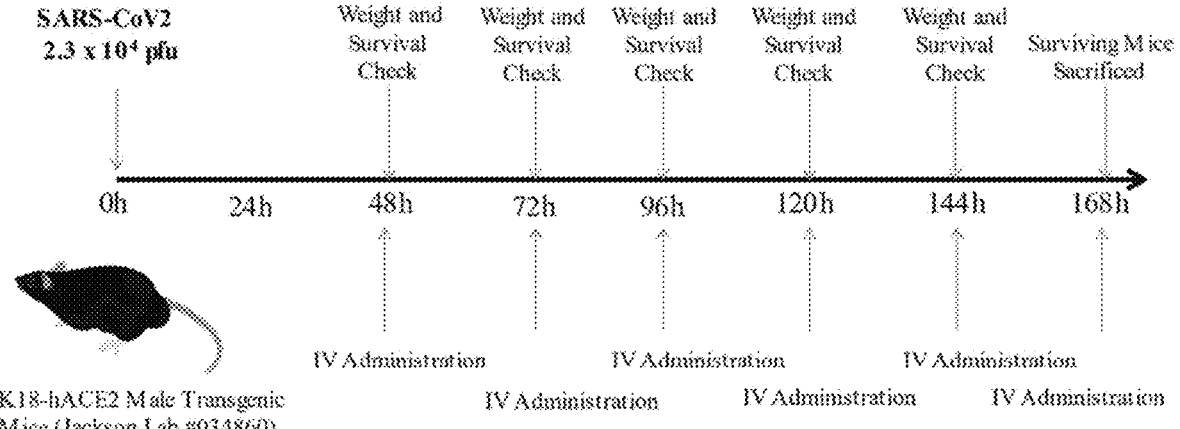

FIG. 34 shows an alternative formulation of CAR-liposome enhancement of dexamethasone. To demonstrate CAR-liposome enhancement of dexamethasone (Dex), SARS—Cov2 infected K18-hACE2 mice could receive hydrocortisone 0.15 mg/kg/dose iv every 24 hours. Liposomes will be formulated and validated as described in FIG. 31, with 4 groups divided as follows: Group 1 (Placebo)—will receive saline injected iv every 24 hours; Group 2 (Dex)—will receive dexamethasone 0.15 mg/kg/dose iv every 24 hours; Group 3 (Dex Lip)—will receive liposome encapsulated dexamethasone 0.15 mg/kg/dose iv every 24 hours; Group 4 (CAR-Lip+Dex)—will receive CAR-liposome encapsulated dexamethasone 0.15 mg/kg/dose iv every 24 hours.

Figure 35:
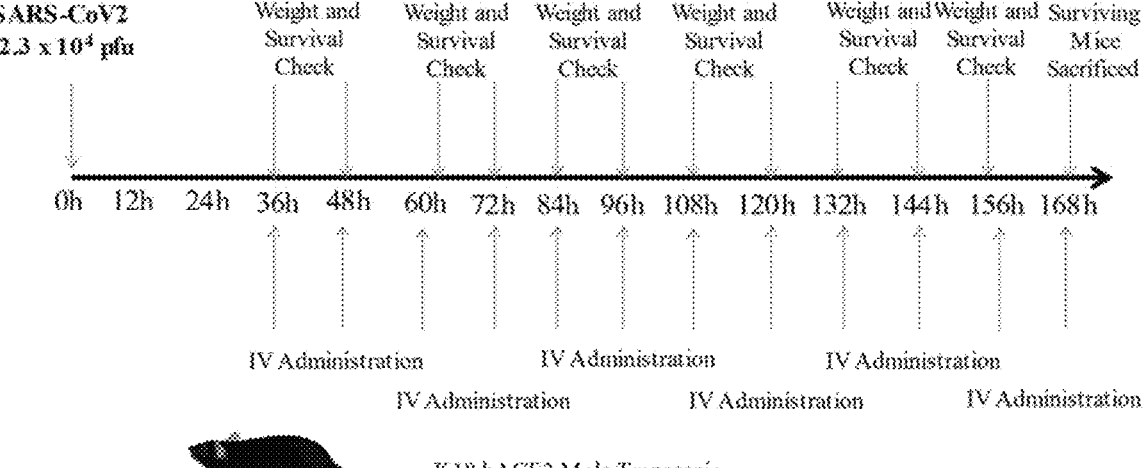

FIG. 35 shows an alternative formulation of CAR-liposome enhancement of methylprednisolone. To demonstrate CAR-liposomes enhancement of methylprednisolone (MPS), SARS—Cov2 infected K18-hACE2 mice could receive methylprednisolone 2 mg/kg twice daily (every 12 hours). Liposomes will be formulated and validated as described above: Group 1 (Placebo)—will receive saline iv.; Group 2 (MPS)—will receive MPS 2 mg/kg/dose iv every 12 hours; Group 3 (MPS Lip)—will receive liposome encapsulated MPS 2 mg/kg/dose iv every 12 hours; Group 4 (CAR-Lip+MPS)—will receive CAR-liposome encapsulated MPS 2 mg/kg/dose iv every 12 hours.

Figure 36:
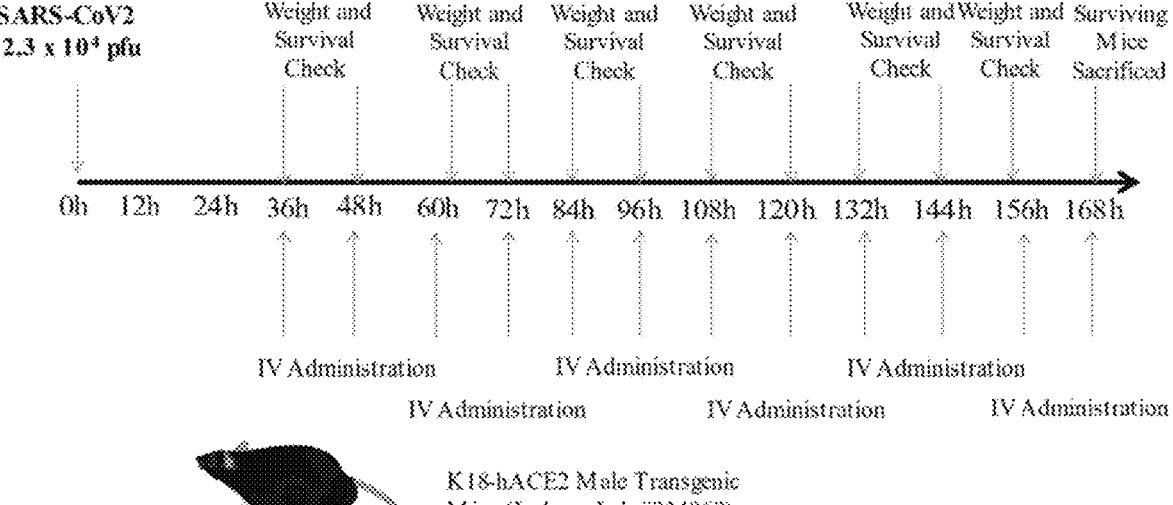

FIG. 36 shows an alternative formulation of CAR-liposome enhancement of hydrocortisone. To demonstrate CAR-liposome enhancement of hydrocortisone (HCT), SARS—Cov2 infected K18-hACE2 mice could receive hydrocortisone 0.2 mg/kg four times daily (every 6 hours). Liposomes will be formulated and validated as described above: Group 1 (Placebo)—will receive saline iv; Group 2 (HCT)—will receive HCT 0.2 mg/kg/dose iv every 12 hours; Group 3 (HCT Lip)—will receive liposome encapsulated HCT 0.2 mg/kg/dose iv every 12 hours; Group 4 (CAR-Lip+HCT)—will receive CAR-liposome HCT 0.2 mg/kg/dose iv every 12 hours.

DETAILED DESCRIPTION OF THE INVENTION

Coronaviruses such as SARS-CoV1, MERS (Middle East respiratory syndrome-related coronavirus), and SARS-CoV2, have recently emerged as major threats to human health. COVID-19, the disease caused by infection with SARS—CoV2 can be viewed as a disease of the glycocalyx, the carbohydrate inner layer of the vascular endothelium. Coronaviruses like SARS-CoV2 and its many variants (B.1.1.7, B.1.351, P.1 and other emerging strains) infect organisms and cause glycocalyx alterations similar to other glycocalyx pathological conditions like sepsis, ARDS, diabetes, heart disease, obesity, lung diseases, kidney disease, liver disease and other conditions. Not coincidentally, these same underlying conditions put an individual at higher risk of serious disease and death upon SARS-CoV2 infection. SARS-CoV2 infection causes vasculitis-like inflammation of blood vessels throughout the organism of individual including the heart, lungs, kidneys, brain, gastrointestinal tract, skin, toes, hands and feet. This SARS-CoV2 infection-related inflammation, generated by the immune system to fight the virus, causes damage to the endothelial glycocalyx including and especially denudation of the glycocalyx in the inflamed tissues and organs. This inflammation and dysfunctional glycocalyx and damaged endothelium can in turn lead to organ failure, neurological and cognitive problems, long term dysfunction and disability known as "Long-haul COVID," sepsis, ARDS and death.

A damaged and denuded glycocalyx phenotype has been previously been identified as the homing target of CAR-SKNKDC (CAR) peptide and its pharmacophore in other diseases. CAR peptide homes to areas of damaged glycocalyx and enables co-administered or conjugated therapies to selectively accumulate in the inflamed target tissues to increase the therapeutic index deliver targeted therapies. Due to CAR peptide's ability to target inflamed tissues, CAR peptide could be an invaluable tool in the search for effective coronavirus therapies. Drugs co-administered or conjugated with CAR peptide such as steroids, antivirals, antibodies, IL-6 receptor antagonists, interferons, JAK inhibitors, and other drugs will selectively accumulate in the COVID-inflamed vessels and tissues to achieve improved localized concentrations of the drug resulting in improved outcomes, especially survival. Since CAR peptide homes to the COVID-inflamed vessels, tissues and organs, CAR peptide can also be used as a targeting moiety on imaging agents to determine the presence, extent and location of injury in COVID inflamed organs and tissues as well as diagnosis, prognosis and disease staging. CAR peptide-targeted imaging agents can be utilized to help patients suffering from "Long-haul COVID" by imaging COVID inflamed tissues to determine the existence, extent of long-term inflammatory effects of COVID infection on tissues and organs.

The potential uses and benefits of CAR peptide for coronavirus diseases can be best illustrated in the following examples. While the following examples highlight COVID-19 disease as a consequence of SARS-CoV2 infection, they can be also applied to disease resulting other coronaviruses:

EXAMPLES

I. The Mechanism of CAR Homing is Enhanced Selective Macropinocytosis at Sites of Damaged Endothelium that Enhance Cellular Uptake of Co-Administered Drugs.

In previous experiments, cell-surface heparan sulfate (HS) was shown to be necessary for both CAR binding and internalization. When treated with heparinase I and III, binding of CAR to Chinese hamster ovary cells was greatly reduced. This suggested that CAR's specific binding and internalization is mediated by the presence of HS moieties on the surface of the target cell. Macropinocytosis is a non-clathrin, non-caveolin, lipid raft-dependent form of endocytosis that allows for the regulated internalization of extracellular solute molecules. Studies have described the role of heparan sulfate as the receptor for lipid raft-dependent macropinocytotic internalization (FIG. 1(A)), and macropinocytosis has also been shown to underlie the internalization of other cationic cell-penetrating peptides (FIG. 1(B)-(D)). Accordingly, heparan sulfate mediated macropinocytosis could explain CAR's ability to increase the local-

13

Figure 1:
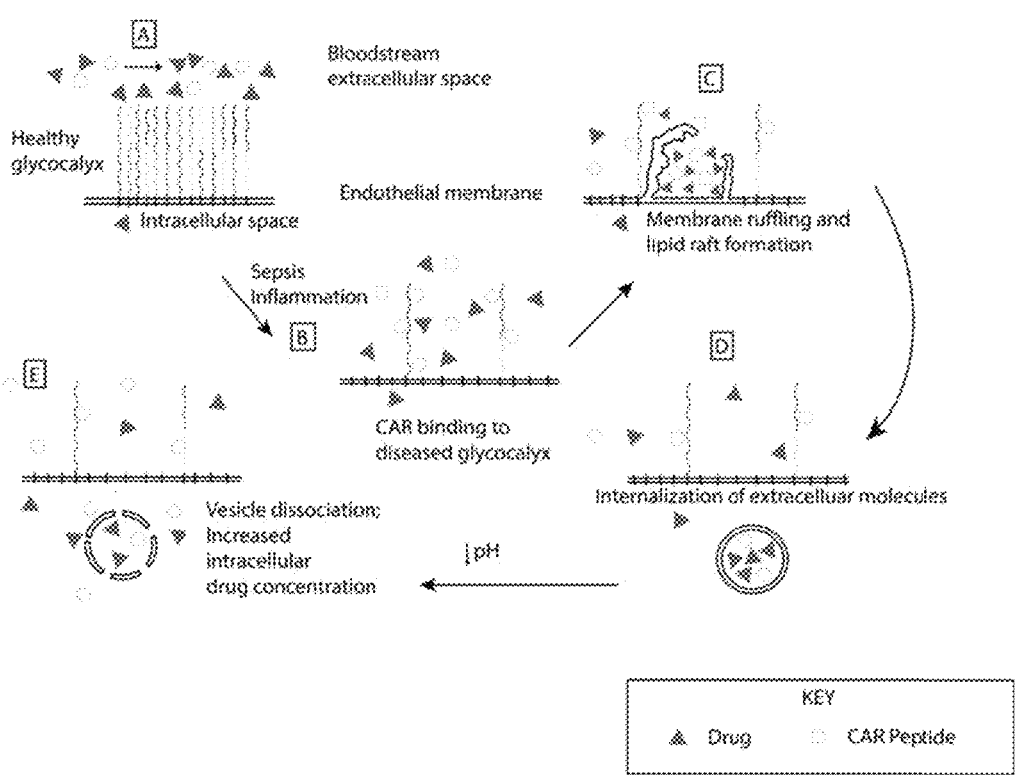
FIG. 1 shows one hypothesized mechanism of action of the present invention. (A) Healthy glycocalyx of endothelial membranes does not bind CAR peptide. Some drug molecules passively diffuse through the plasma membrane but majority of drug remains in bloodstream. (B) After sepsis injury, heparanase expression causes selective enzymatic cleavage of heparan sulfate chains and modification of the glycocalyx. HS variants resistant to cleavage remain intact, allowing CAR to bind to its HS receptors. (C) Binding of CAR triggers membrane ruffling and lipid raft formation, causing inward folding of the plasma membrane and engulfing of extracellular components including CAR and drug molecules. (D) Macropinocytic vesicles containing CAR and drug molecules are internalized into the cell. (E) Reduced intracellular pH causes the macropinosome to dissociate, releasing CAR and drug into the cell.

14 ized concentration of co-administered drugs without requiring the drugs to be conjugated to CAR (FIG. 1(E)).

II. CAR Administration is Safe, Even at High Doses.

Recent standalone safety pharmacology studies were performed by Charles River Labs to define the dose-response relationship of CAR and screen for potentially adverse effects of CAR on vital physiological systems in rats found no adverse effects even at the highest levels of CAR tested. A TID 10-Day rising-dose and multiple-dose tolerance study of CAR peptide administration in rats found no mortality, adverse clinical observations, and no aberrations in hematology, coagulation or clinical chemistry even at the highest CAR dose tested of 20 mg/kg IV. Similarly, no adverse effects of CAR administration were observed in behavior and physiological function in an Irwin test in rats. Separately, two-month long repeat-administration of CAR to pigs at IV dose of 3 mg/kg revealed no immunological effects or signs of toxicity.

III. CAR Selectively Targets and Penetrates Sites of Endothelial Injury in the Lung, Liver and Kidney, but does not Home to Healthy Organs.

It has been previously shown that CAR targets wounds and pulmonary hypertensive vasculature (Urakami T, et al. Peptide-Directed Highly Selective Targeting of Pulmonary Arterial Hypertension. *The American Journal of Pathology.* 2011; 178(6):2489-2495; Toba M, et al. A Novel Vascular Homing Peptide Strategy to Selectively Enhance Pulmonary Drug Efficacy in Pulmonary Arterial Hypertension. *The American Journal of Pathology.* 2014; 184(2):369-375; Patel G P, et al. Systemic steroids in severe sepsis and septic shock. Am J Respir Crit Care Med. 2012; 185:133-139).

Figure 2A:
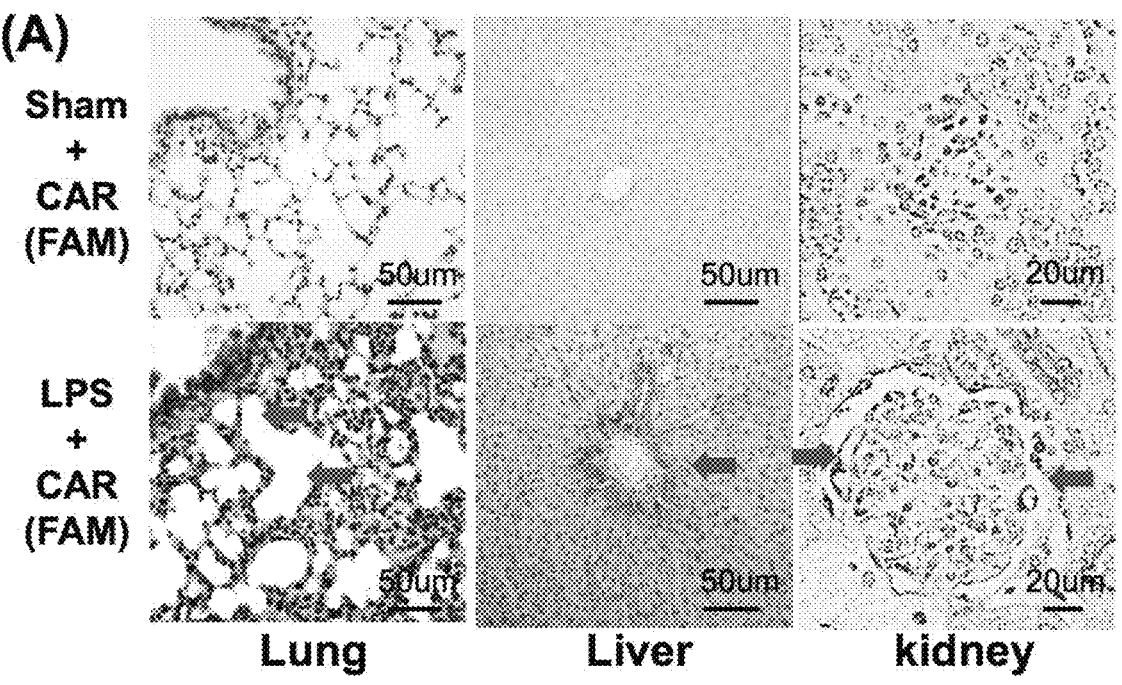
FIG. 2 shows CAR was transported to lung, liver and kidney vessels in LPS-induced endotoxemia. (A) FAM-CAR peptide was not detected anywhere in sham mice, except for uriniferous tubules where CAR peptide is excreted. FAM-CAR peptide was detected after LPS in lung, liver and kidney (red arrows). (B) Double immunofluorescence staining demonstrated CAR co-localization to glomerular endothelium after LPS but not in sham mice.

Homing properties of CAR peptide has been demonstrated in an LPS model of endotoxemia. 10-week-old C57BL/6 male mice, which were given an intraperitoneal (IP) injection of *Escherichia coli* 055:B5 LPS 20 mg/kg or saline (sham), followed 12 hours later by IP injection of FAM- or FITC-conjugated CAR peptide. Mice were then euthanized 1 hour later. Conjugated FAM-CAR retention was detected in the pulmonary vessels, Glisson's sheath of the liver and glomeruli, and uriniferous tubules of endotoxinemic mice (FIG. 2(A)). In contrast, no CAR was detected in the sham treated animals except for the uriniferous tubules where all proteins below 10,000 Daltons are excreted.

Figure 2B:
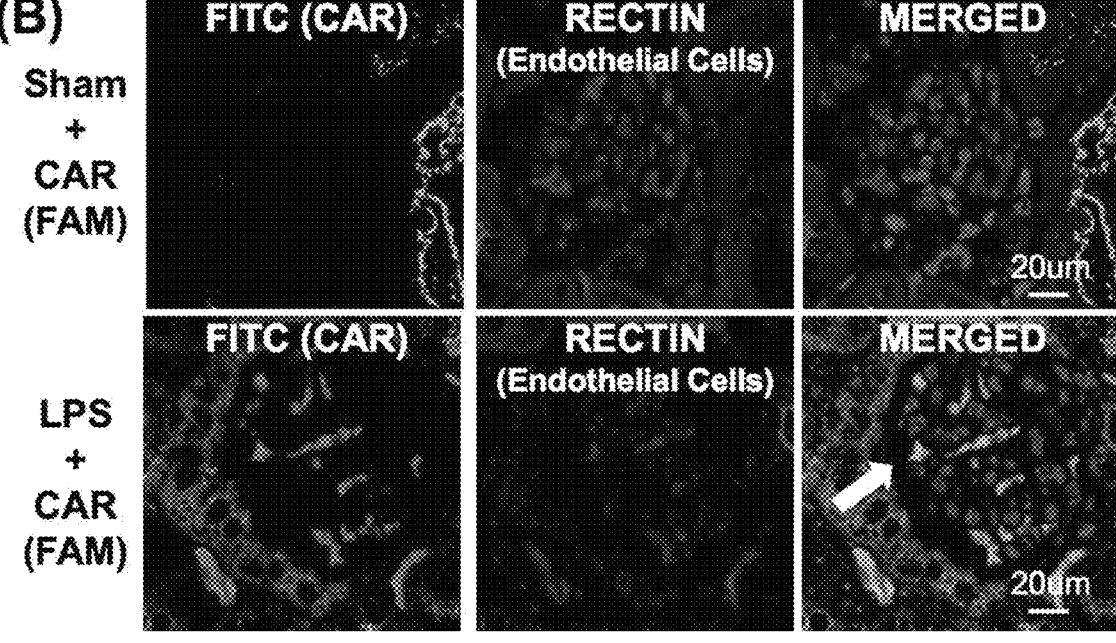

Double immunofluorescence staining co-localized FITC-CAR to the glomerular endothelium in LPS-exposed mice, but not sham mice (FIG. 2(B)). These findings demonstrate that CAR is a homing peptide with high selectivity for LPS-damaged organs, including the lungs, liver and kidneys. This tissue selectivity may offer a novel opportunity to simultaneously target multiple organs that are commonly injured during the systemic inflammatory response in sepsis.

IV. CAR+Low Dose Hydrocortisone Increases Survival after LPS-Endotoxemia in Mice.

10-week-old C57BL/6 male mice were given an intraperitoneal (IP) injection of *Escherichia coli* 055:B5 LPS 20 mg/kg. Mice were injected i.p. with 20 mg/kg lipopolysaccharide (LPS). Five different treatments were initiated: saline only group (Untreated, n=31); CAR peptide-alone administration 20 mg/kg (500 ug total dose) (CAR alone, n=20); hydrocortisone 0.2 mg/kg or 10 mg/kg Low-HCT or High-HCT, n=20, 28 respectively); and CAR 20 mg/kg co-administered with hydrocortisone 0.2 mg/kg (Low HCT+ CAR, n=20). Hydrocortisone and/or CAR peptide were injected intraperitoneally at 3, 12 and 24 hours after LPS administration.

Figure 3:
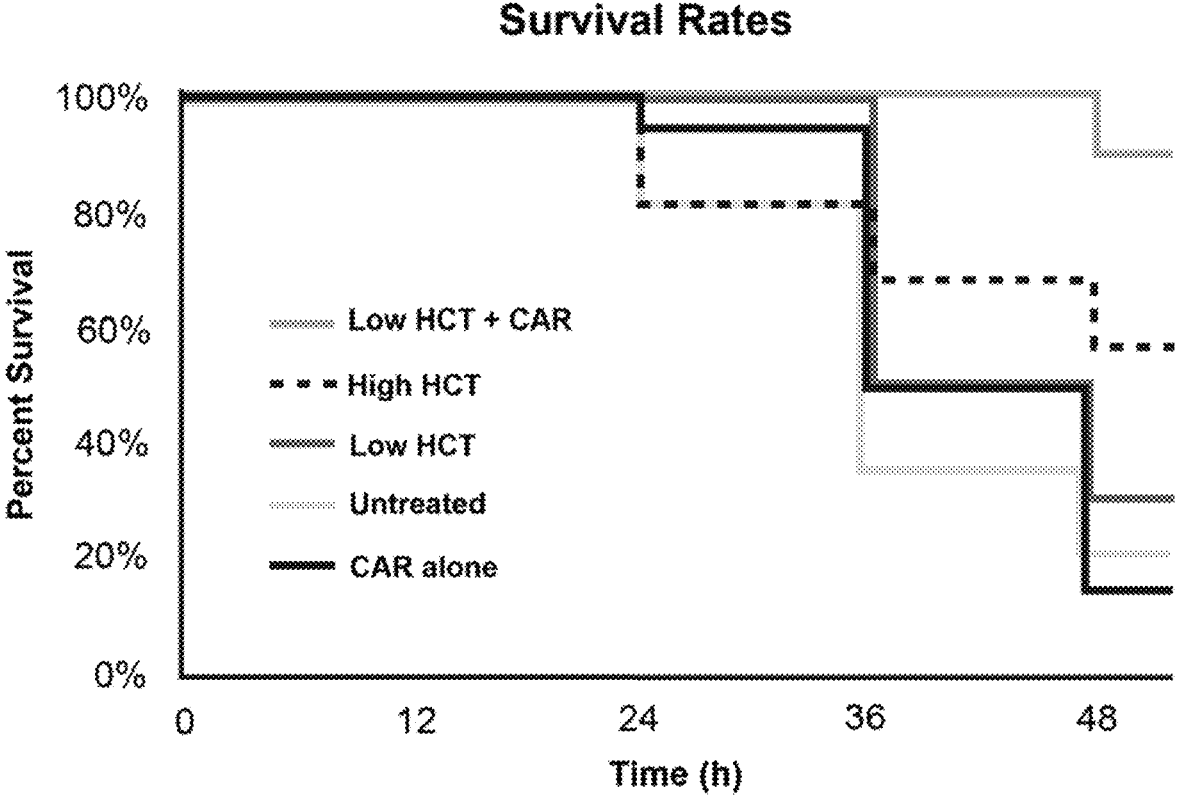
FIG. 3 shows survival rate 48 hours after LPS injection. 48 h after LPS administration, Group CAR+Low-HCT showed the best survival rate compared with untreated sepsis, (90 vs. 21%, p<0.05), and a higher survival rate than Group High HCT. There was no significant survival difference between Groups CAR alone, Low-HCT and untreated sepsis.

Forty-eight hours after LPS administration, Low HCT+ CAR showed the best survival ratio compared with Group S (90 vs. 21%, p<0.05), and High HCT showed a better survival ratio than Untreated (57 vs. 21%, p<0.05). There was no significant survival difference between the CAR alone, Low-HCT and Untreated mice (FIG. 3).

V. Ultrastructural Analysis of the Endothelium and Endothelial Glycocalyx.

Figure 4:
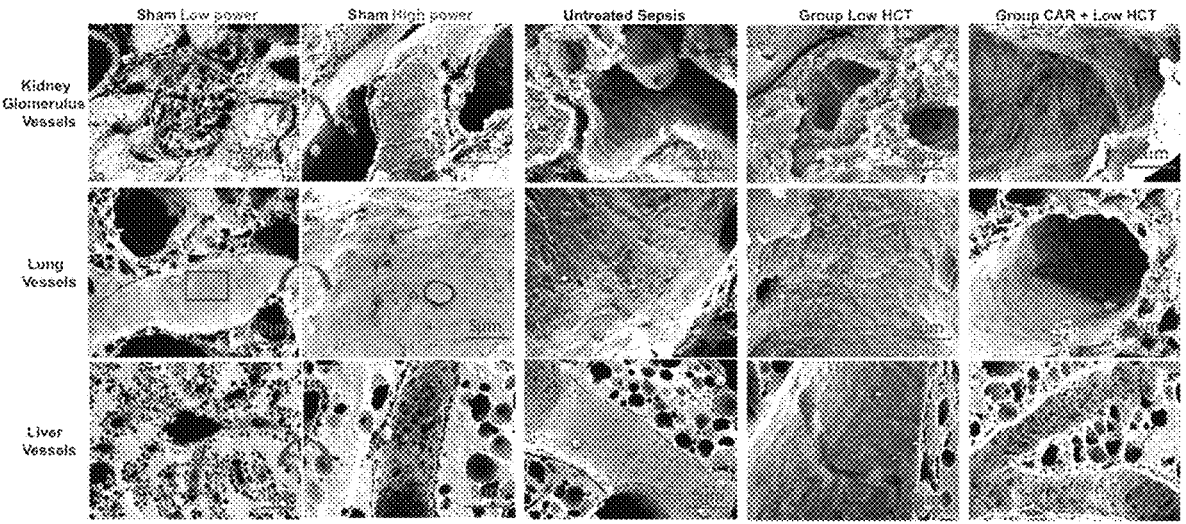
FIG. 4 shows an ultrastructural analysis of endothelium of each organ. Capillaries of the kidney are fenestrated capillaries which have small holes at endothelial cells. The destruction of this structure was 48 hours after LPS injection. Then, the endothelial wall became edematous and there was deposited fibrin on it. Capillaries of the lung are continuous type of capillaries. Although the vascular endothelium of the lung is thinner at the edges of the nucleus, edema occurred and vascular endothelial structure was impaired 48 hours after LPS injection. Capillaries of the liver are sinusoids which have a lot of large intracellular gap in normal capillaries. 48 hours after LPS administration, these structures have already broken the edematous of the vascular endothelium and deposited fibrin. Treatment of 0.2 mg/kg hydrocortisone has no beneficial effect for septic endothelial disorders. On the other hand, Hydrocortisone with CAR therapy attenuated endothelial injuries.
Figure 5:
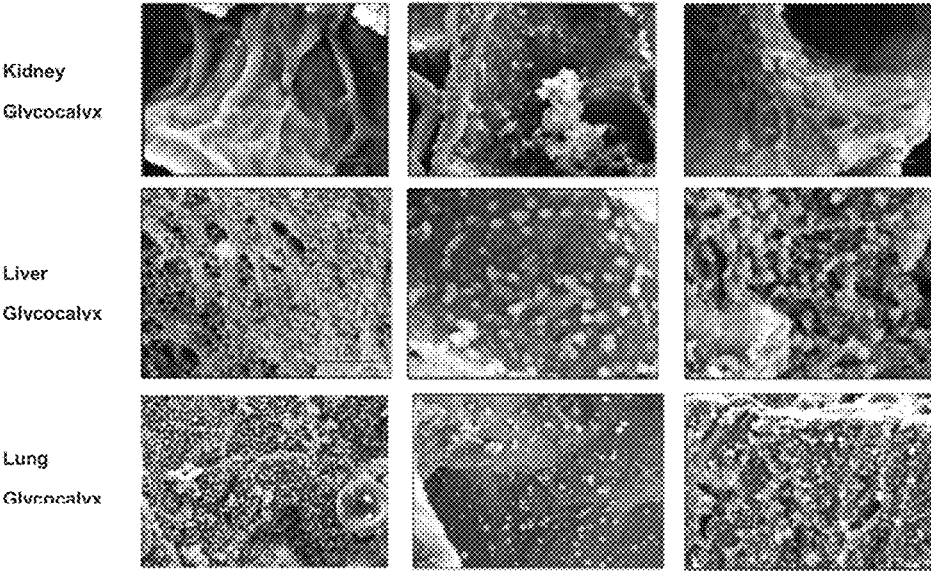
FIG. 5 shows another ultrastructural analysis of endothelial glycocalyx of each organ. The endothelial glycocalyx (GCX) of the apical endothelial surface of each organ can by visualized using scanning electron microscopy (SEM) to assess GCX appearance and structure. GCX was largely denuded in the untreated sepsis group but the GXX damage was attenuated when CAR is co-administered with low-HCT. The CAR+Low-HCT GCX is comparable in morphology to the healthy GCX.

Mice were sacrificed at 48 hours after LPS administration, and kidney, lung and liver were obtained to create frozen fracture freeze-dried samples to detect endothelial changes with electron microscopy. The specimens were examined under a scanning electron microscope (S-4500, Hitachi). The endothelial cell structure was different in each organ (FIG. 4), and included three types: fenestrated (kidney), continuous (lung), and sinusoid (liver). The endothelial glycocalyx (GCX) of the apical endothelial surface of each organ was visualized using scanning electron microscopy (SEM) to assess GCX appearance and structure (FIG. 5). In the untreated LPS group, we observed the destruction of lung, kidney and liver capillaries, with edematous endothelial walls and fibrin deposition. In the CAR+Low-HCT group, the destruction of lung, liver and kidney capillaries was markedly attenuated compared with the untreated LPS and Lox-HCT groups. These images demonstrate that CAR co-administration with low dose hydrocortisone rescued damaged endothelial tissue in three very different organs that are involved in the multi-organ failure that is characteristic of sepsis. These results strongly indicate that co-administration of low-dose hydrocortisone and CAR peptide is a highly effective treatment strategy to ameliorate endothelial injury and increase survival in an LPS model of sepsis.

VI. CAR+Hydrocortisone Reverses Endotheliopathy, Improves Hyperglycemia, and Increases Survival after CLP in Rats.

Figure 6:
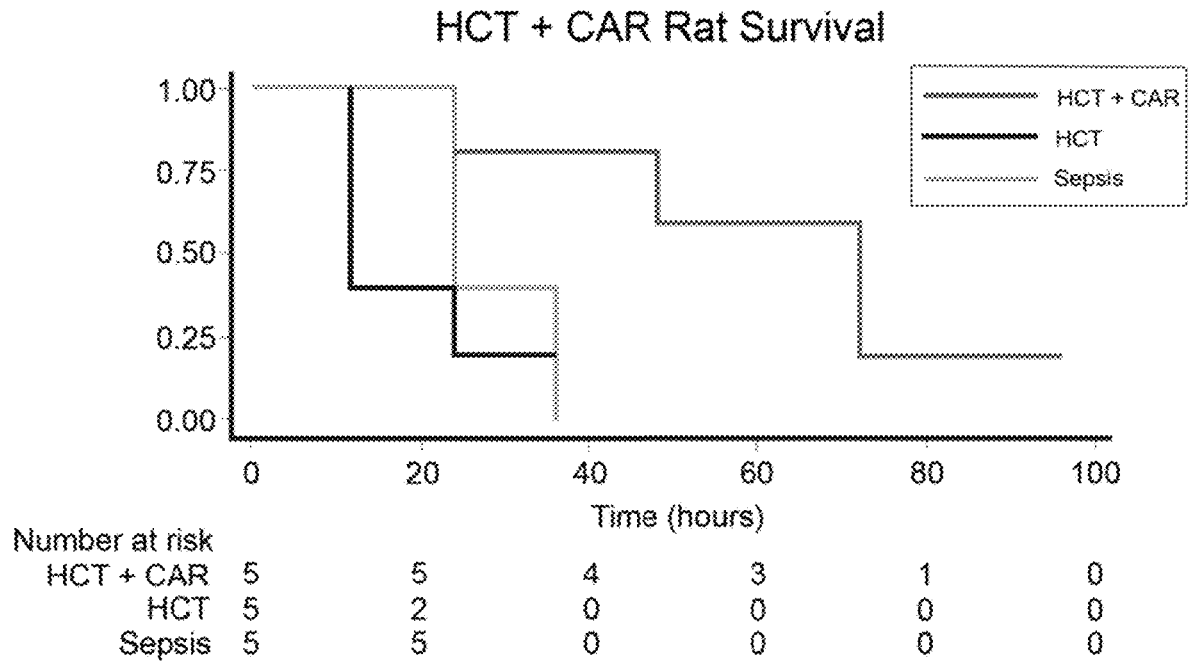
FIG. 6 shows survival in the 2CLP rat model of sepsis: Only rats in the HCT+CAR group survived 40 hours and beyond. At 40 hours, 4 of the 5 rats in the HCT+CAR group survived while none of the rats in either the HCT group nor the sepsis group survived for 40 hours (n=5 in each group) (Log-rank P=0.008).

8-10 week-old male Sprague Dawley rats were exposed to CLP. Rats were randomized (n=5/group) to saline, hydrocortisone (0.2 mg/kg IV), or CAR (3 mg/kg IV)+HCT. Treatments were initiated 12 hours after surgery, and given every 12 hours afterwards until death, for a maximum of 5 days. Rats were treated with fluid resuscitation but not with antibiotics in this model. Survival was highest in the CAR+ HCT group (FIG. 6) (Log-rank P=0.008) and the median Ang2/Ang1 ratio was lower in CAR+HCT than the hydrocortisone group (0.60 vs 1.69, p=0.06). In addition, CAR+ HCT avoided the hyperglycemia observed after HCT alone, suggesting that CAR may be able to limit undesirable effects of HCT that expose to harm.

VII. Co-Administered CAR Markedly Increased Imatinib Levels in PAH Lung Tissue Compared with Imatinib Alone.

Figure 7:
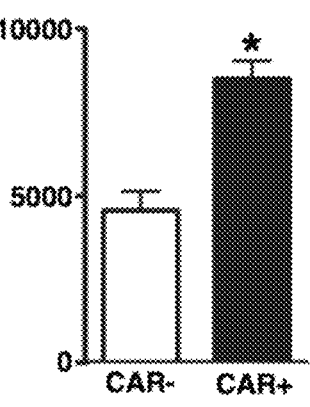
FIG. 7 shows imatinib content (ng) in 1 g lung tissue after addition of 3 mmol/L imatinib with (+) and without (−) 1 mg CAR to 30 mL perfusate of isolated perfused lungs from SU/Hx/Nx rats. N=5 and 4 for CAR+ and CAR− respectively. P<0.05 versus CAR−.

The ability of CAR to enhance drug uptake in the target tissue was assessed in a preclinical model of pulmonary arterial hypertension, a condition similarly characterized by damaged endothelium. To examine whether CAR increases drug transport into the hypertensive lungs, we measured tissue concentrations of imatinib in isolated, salt solution perfused PAH lungs. Results indicated a significant increase in the levels of imatinib detected with CAR compared to without CAR (FIG. 7).

VIII. Corticosteroids Bind to Intracellular Receptors and Prevent Synthesis of Inflammatory Agents.

Within the cytoplasm, there are glucocorticosteroid receptors (GR). These receptors bind to corticosteroids and prevent the synthesis of inflammatory agents. When the corticosteroids bind to the receptor, the hormone-receptor complex moves to the nucleus of the cell. This complex inhibits the proteins that acetylate histones called histone acetyltransferases (HATs) and activate histone deacetylases (HDACs) which remove acetyl groups. Acetylation of histones makes it easier for DNA transcription to occur, resulting in the synthesis of more inflammatory proteins. The deacetylation of regions of DNA encoding for inflammatory agents results in the down regulation of many inflammatory agents such as IRF3 transcription factor, implicated in interferon production. The hormone-receptor complex also inhibits pro-inflammatory proteins by increasing the synthesis of IκBα which binds to NF-κB and sequestering it in the cytoplasm. Upon activation, NF-κB is implicated in the production of pro-inflammatory cytokines when it travels to the nucleus. IκBα binding prevents its translocation to the nucleus. This results in the limitation of the inflammatory factors NF-κB produces by the cell.

IX. CAR Co-Administered with Sivelestat and Anti-Thrombin III Dramatically Increased Survival Rates in an LPS Model of Sepsis Compared to Controls and Sivelestat and Anti-Thrombin III Monotherapies.

Figure 8:
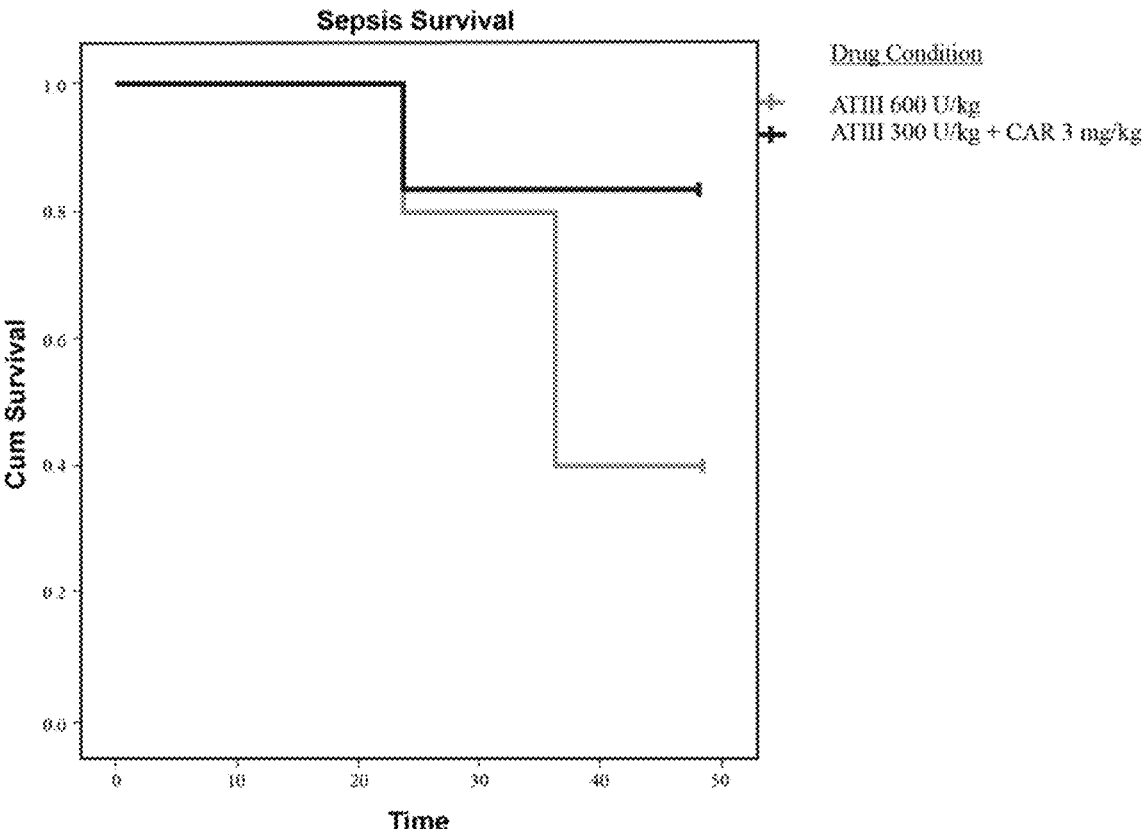
FIG. 8 shows CAR dramatically improves survival in septic mice treated with anti-thrombin III (ATIII). Sepsis was initiated and survival measured as in FIG. 1, with doses given at 3 and 24 hours to match the clinical use of ATIII. At 48 hours, the survival rate of CAR+ATIII treated animals was 83% compared to 50% in control and 40% in ATIII only groups, representing a 66% increase in survival of CAR treated animals over the ATIII only group. The decreased survival of ATIII only animals could be due to hemorrhage caused by ATIII's anti-coagulant activity. CAR appeared to completely reverse this effect.
Figure 9:
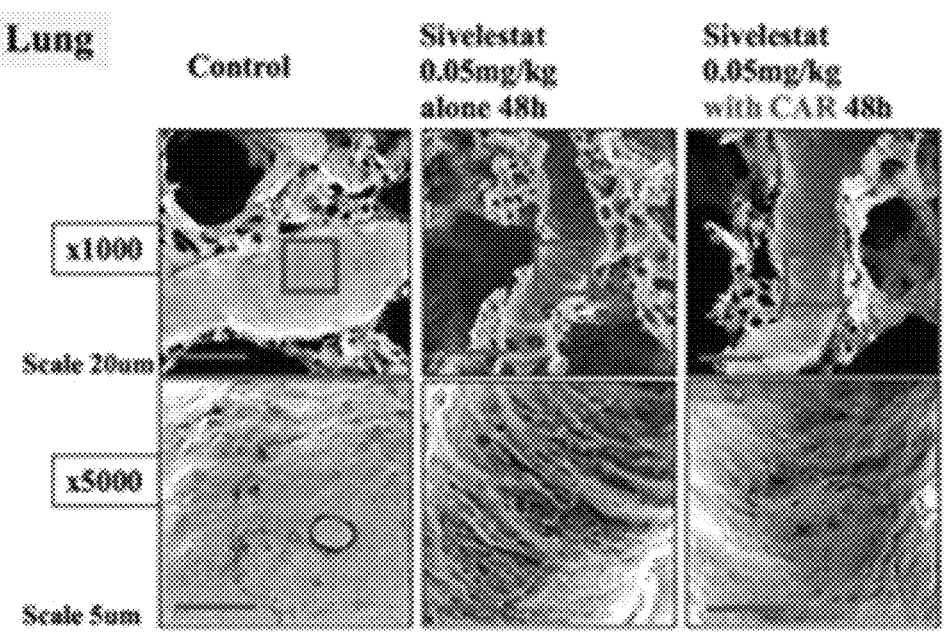
FIG. 9 shows SEM lung images. Scanning electron micrographs of lung tissue from control, sivelestat alone, and CAR+sivelestat treated animals. The pulmonary vasculature is shown in the enlargement. Sivelestat alone did not prevent degradation of the continuous pulmonary arteriole endothelium. When CAR is co-administered with sivelestat, degradation of the endothelium is prevented, and its continuous appearance is similar to control.
Figure 10:
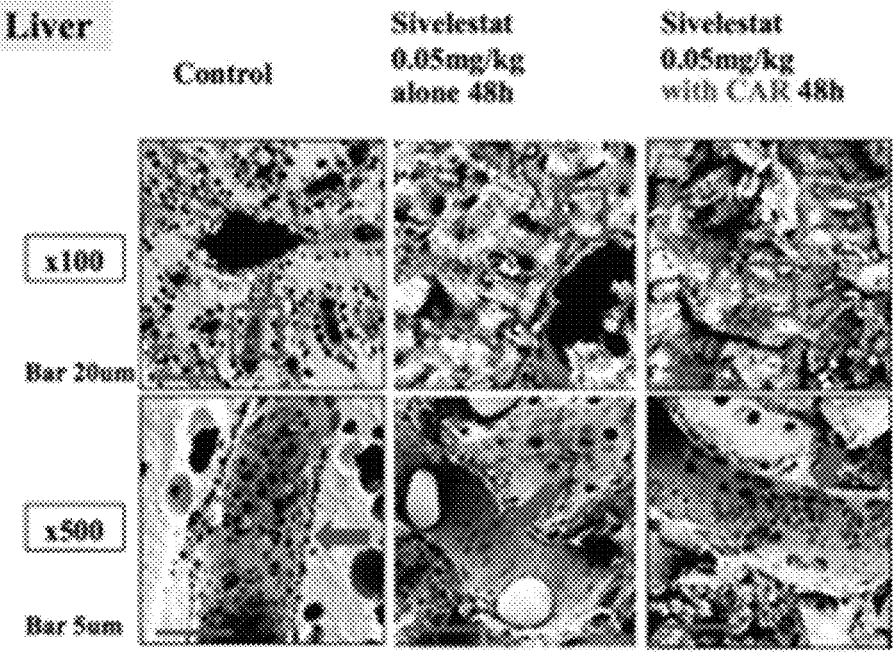
FIG. 10 shows SEM liver images. Scanning electron micrographs of liver tissue from control, sivelestat alone, and CAR+sivelestat treated animals. The fenestrated sinusoidal endothelium with clusters of fenestrations, or 'sieve plates,' are visible in the control liver vasculature. Sivelestat alone is not able to prevent defenestration of sieve plates in septic animals. When CAR is co-administered with sivelestat to septic animals, the size and number of sieve plate clusters is restored to almost control levels.
Figure 11:
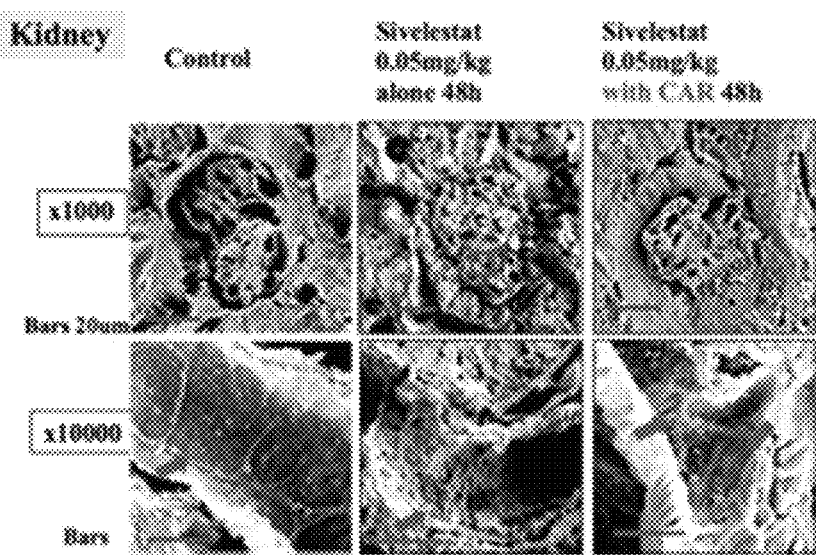
FIG. 11 shows SEM kidney images. Scanning electron micrographs of kidney tissue from control, sivelestat alone, and CAR+sivelestat treated animals. In the enlargement shown of the hepatic vasculature, the fenestrated glomerular endothelium surrounded by podocyte foot processes (red arrow). In septic animals treated with sivelestat alone, the fenestrations are absent and gross tissue damage is apparent (red arrow). This is presumably due to activation of neutrophil elastase which leads to proteolytic degradation of critical extracellular matrix proteins. When co-administered with CAR, the fenestrations are restored to almost control levels (red arrow). The activity of sivelestat's anti-elastase appears to be efficiently boosted by CAR's selective homing to the injured endothelial glycocalyx in the kidney.

Similar to the hydrocortisone therapy, CAR in combination with sivelestat and anti-thrombin 3 treatment displayed dramatically improved survival rates compared to the controls and monotherapy alone (Table 1 and Table 2; FIG. 8). Thus, CAR could potentially adjuvant efficacy of other drugs against viral sepsis, including CAR in combination with sivelstat, as shown at lung (FIG. 9), liver (FIG. 10) and kidney (FIG. 11) samples.

TABLE 1

Sepsis survival rates with sivelestat treatment
Survival Rate (%)

| | 12 h | 24 h | 36 h | 48 h |
|---|---|---|---|---|
| LPS only (n = 20) | 100 | 95 | 75 | 50 |
| Sivelestat 0.5 mg/kg (n = 20) | 100 | 85 | 60 | 50 |
| Sivelestat 0.5 mg/kg + CAR (n = 18) | 100 | 100 | 89 | 89 |

TABLE 2

Sepsis survival rates with anti-thrombin III treatment
Survival Rate (%)

| | 12 h | 24 h | 36 h | 48 h |
|---|---|---|---|---|
| LPS only (n = 14) | 100 | 93 | 79 | 50 |
| ATIII 600 U/kg (n = 10) | 100 | 80 | 40 | 40 |
| ATIII 300 U/kg + CAR (n = 12) | 100 | 83 | 83 | 83 |

X. CAR could Potentially Act as an Adjuvant for Anti-Viral Therapies for COVID-19 Patients.

CAR has shown increased survival in sepsis models when co-administered with three different drugs (HCT, sivelestat, and ATIII). CAR has also shown the ability to target and penetrate organ cells only in cases of endothelial injury. Based on these findings, CAR could potentially adjuvant anti-viral therapies such as remdesivir. In addition to attacking cells characterized by immune response or endothelial injury CAR could attack and home to cells affected by COVID-19 and increase localized activity of co-administered drugs.

XI. Preliminary Tolerability Studies of CAR in Healthy Animals.

We have investigated the impact of repeated dosing of CAR peptide at exposures previously determined to be effective in augmenting pulmonary vasodilator responses of fasudil, imatinib and sildenafil, i.e., 3 mg/kg/d by intravenous or sublingual routes in rat models of pulmonary hypertension. In healthy adult Sprague-Dawley rats, we found that administration of intravenous CAR peptide at a dose of 3 mg/kg i.v. for 14 days had no impact on blood renal function tests (creatinine, blood urea nitrogen), hepatic function tests (AST, alkaline phosphatase, total bilirubin), hematologic tests (hemoglobin and white cell count) and glucose hemostasis (Table 3).

TABLE 3

Tolerability of CAR in healthy animals

| | Control | CAR |
|---|---|---|
| Creatinine (mg/dL) | 0.46 ± 0.03 | 0.45 ± 0.02 |
| BUN (mg/dL) | 17 ± 1 | 17 ± 1 |
| AST(U/L) | 111 ± 17 | 141 ± 31 |
| ALP (U/L) | 180 ± 27 | 170 ± 18 |
| Tbili (mg/dL) | 0.08 ± 0.02 | 0.10 ± 0.04 |
| Hb (g/dL) | 12.8 ± 0.3 | 12.8 ± 0.2 |
| Wbc (×1000/μL) | 4.4 ± 0.6 | 4.0 ± 0.7 |
| Glucose (mmol/L) | 221 ± 20 | 213 ± 5 |

In summary, these data demonstrate that CAR peptide safely homes to damaged endothelium in multi-organ failure, ARDS, and sepsis, and induces localized macropinocytosis that selectively augments drug uptake in damaged organs such that CAR+HCT reverses endothelial and glycocalyx injury, and increases survival better than HCT alone in both a LPS mouse model of endotoxemia and a 2CLP rat model of sepsis. In addition, our data shows that CAR+ sivelestat and CAR+ATIII increase survival better than sivelestat or ATIII on their own in an LPS model. Thus, CAR peptide can be used as an adjuvant with multiple coronavirus drugs, viral sepsis drugs, anti-viral drugs to improve the effectiveness of these drugs in COVID-19 patients.

The following examples are further studies to be conducted in order to validate the above-described examples.

A. CAR+Steroids for COVID Animals and Humans Resulting in Improved Survival & Reduced Hyperglycemia & Cachexia.

In a proof-of-concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3 \times 104$ plaque-forming units. The lethality of the disease model can be modified by altering the volume of virus titer administered to the K18-hACE2 mice, with the 50% lethal dose of SARS-CoV for K18-hACE2 mice was less than 230 plaque-forming unit after intranasal inoculation. SARS-Cov2 infected K18-hACE2 mice also suffer rapid weight loss with lethargy and labored breathing.

In an initial experiment to demonstrate the utility of CAR peptide for treating COVID-19 disease in humans, we will take 60 K18-hACE2 male transgenic mice (Jackson Lab #034860) and administer intranasal inoculations of SARS-CoV2 at $2.3 \times 10^4$ plaque-forming units to each mouse and divide them into 3 equal-sized treatment groups of 20 mice each:

Group 1 (Placebo)—will receive placebo (PBS) injections ip every 24 hours

Group 2 (Dex)—will receive Dexamethasone 0.15 mg/kg/ dose ip every 24 hours

Figure 12:
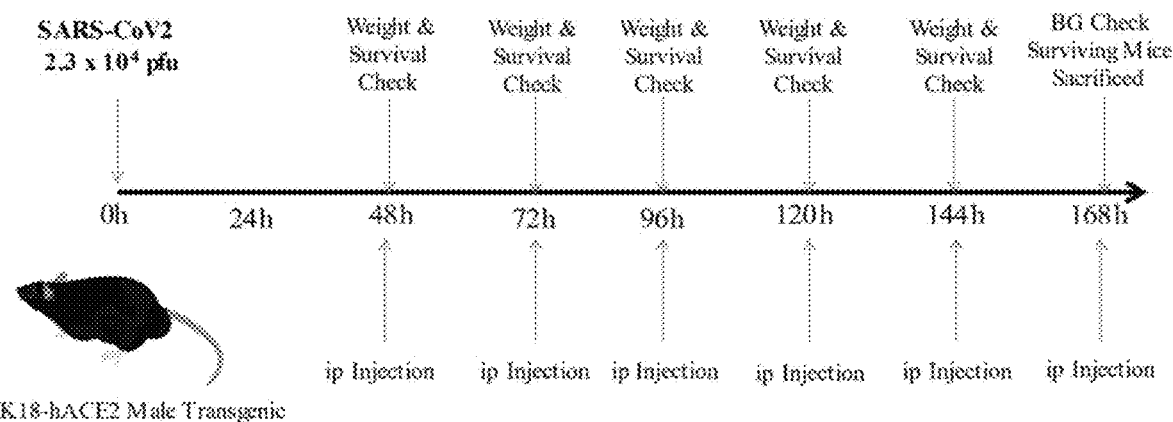
FIG. 12 shows CAR+dexamethasone in a COVID-19 animal model. 60 K18-hACE2 male transgenic mice are used with administration of intranasal inoculations of SARS-CoV2 at $2.3 \times 10^4$ plaque-forming units to each mouse to occur before dividing them into 3 equal-sized treatment groups of 20 mice each: Group 1 (Placebo)—will receive placebo (PBS) injections ip every 24 hours; Group 2 (Dex)—will receive Dexamethasone 0.15 mg/kg/dose ip every 24 hours; Group 3 (CAR+Dex)—will receive Dexamethasone 0.15 mg/kg/dose ip every 24 hours co-administered with CAR peptide administered ip 8 mg/kg every 24 hours.

Group 3 (CAR+Dex)—will receive Dexamethasone 0.15 mg/kg/dose ip every 24 hours co-administered with CAR peptide administered ip 8 mg/kg every 24 hours (FIG. 12).

Prior to initiation of the experiment, we will weigh the mice and determine the baseline blood glucose levels of the mice after a morning 6 hour fast from 8 am to 2 pm with water allowed. Other than fasting periods, mice will be fed and watered ad libitum. After baseline blood glucose levels and weights have been established, we will inoculate mice on Day 0 dpi, and initiate the respective treatments on day 2 dpi and continue with daily ip injections for the entire 7-day experiment. All mice will be checked for survival and weighed daily. On day 7 dpi all surviving mice will undergo a 6-hour morning fast with water allowed, have their blood glucose level and weight determined, be sacrificed, and relative survival, weights and blood glucose levels determined.

At 7 dpi we predict to observe near 100% lethality in Group 1 (Placebo), some improvements in survival in Group 2 (Dex), but significantly increased survival in Group 3 (CAR+Dex) mice relative to both Groups 1 & 2. We would also expect to observe amelioration of weight loss in the Group 3 mice relative to Groups 1 & 2.

We would also expect to observe lower incidence of hyperglycemia and lower blood glucose levels in Group 3 relative to Group 2.

Figure 13:
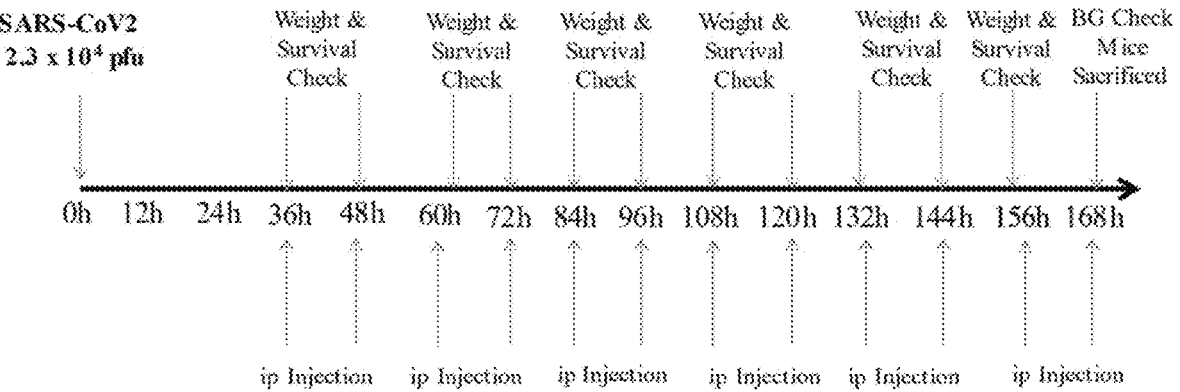
FIG. 13 shows CAR+methylprednisolone in a COVID-19 animal model. This model demonstrates CAR enhancement of methylprednisilone (MPS). 60 K18-hACE2 male transgenic mice are to be used, with administration of intranasal inoculations of SARS-CoV2 at $2.3 \times 10^4$ plaque-forming units to each mouse to occur before dividing them into 3 equal-sized treatment groups of 20 mice each. Group 1 (Placebo)—will receive placebo (PBS) injections; Group 2 (MPS)—will receive methylprednisolone 2 mg/kg dose ip every 12 hours; Group 3 (CAR+MPS)—will receive methylprednisolone 2 mg/kg dose ip every 12 hours co-administered with CAR peptide administered ip 8 mg/kg every 12 hours.
Figure 13:

With an alternate steroid, methylprednisolone, we will demonstrate CAR enhancement of methylprednisilone (MPS). We will take 60 K18-hACE2 male transgenic mice (Jackson Lab #034860) and administer intranasal inoculations of SARS-CoV2 at $2.3\times10^4$ plaque-forming units to each mouse and divide them into 3 equal-sized treatment groups of 20 mice each:

Group 1 (Placebo)—will receive placebo (PBS) injections
Group 2 (MPS)—will receive methylprednisolone 2 mg/kg dose ip every 12 hours
Group 3 (CAR+MPS)—will receive methylprednisolone 2 mg/kg dose ip every 12 hours co-administered with CAR peptide administered ip 8 mg/kg every 12 hours (FIG. 13).

Prior to initiation of the experiment, we will weigh the mice and determine the baseline blood glucose levels of the mice after a morning 6 hour fast from 8 am to 2 pm with water allowed. Other than fasting periods, mice will be fed and watered ad libitum. After baseline blood glucose levels and weights have been established, we will inoculate mice on Day 0 dpi, and initiate the respective treatments on day 2 dpi and continue with daily ip injections for the entire 7 day experiment. All mice will be checked for survival and weighed daily. On day 7 dpi all surviving mice will undergo a 6-hour morning fast with water allowed, have their blood glucose level and weight determined, be sacrificed, and relative survival, weights and blood glucose levels determined.

At 7 dpi we predict to observe near 100% lethality in Group 1 (Placebo), some improvements in survival in Group 2 (MPS), but significantly increased survival in Group 3 (CAR+MPS) mice relative to both Groups 1 & 2. We would also expect to observe amelioration of weight loss in the Group 3 mice relative to Groups 1 & 2.

We would also expect to observe lower incidence of hyperglycemia and lower blood glucose levels in Group 3 relative to Group 2.

Figure 14:
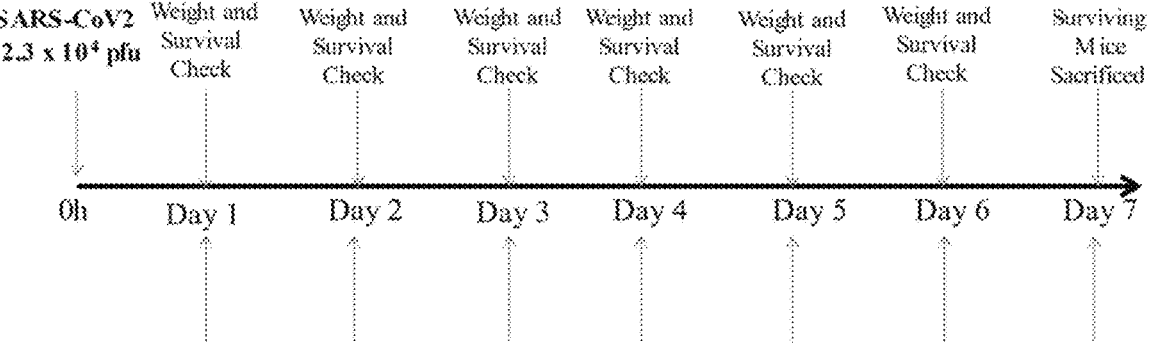
FIG. 14 shows CAR+hydrocortisone in a COVID-19 animal model. This model demonstrates CAR enhancement of hydrocortisone (HCT). 60 K18-hACE2 male transgenic mice are to be used, with administration of intranasal inoculations of SARS-CoV2 at $2.3 \times 10^4$ plaque-forming units to each mouse to occur before dividing them into 3 equal-sized treatment groups of 20 mice each. Group 1 (Placebo)—will receive placebo (PBS) injections; Group 2 (HCT)—will receive hydrocortisone 0.2 mg/kg dose ip every 6 hours; Group 3 (CAR+HCT)—will receive hydrocortisone 0.2 mg/kg dose ip every 6 hours co-administered with CAR peptide administered ip 8 mg/kg every 6 hours.
Figure 14:

With another steroid, hydrocortisone, we will demonstrate CAR enhancement of hydrocortisone (HCT). We will take 60 K18-hACE2 male transgenic mice (Jackson Lab #034860) and administer intranasal inoculations of SARS- CoV2 at $2.3\times10^4$ plaque-forming units to each mouse and divide them into 3 equal-sized treatment groups of 20 mice each:

Group 1 (Placebo)—will receive placebo (PBS) injections
Group 2 (HCT)—will receive hydrocortisone 0.2 mg/kg dose ip every 6 hours
Group 3 (CAR+HCT)—will receive hydrocortisone 0.2 mg/kg dose ip every 6 hours co-administered with CAR peptide administered ip 8 mg/kg every 6 hours (FIG. 14).

Prior to initiation of the experiment, we will weigh the mice and determine the baseline blood glucose levels of the mice after a morning 6 hour fast from 8 am to 2 pm with water allowed. Other than fasting periods, mice will be fed and watered ad libitum. After baseline blood glucose levels and weights have been established, we will inoculate mice on Day 0 dpi, and initiate the respective treatments on day 2 dpi and continue with daily ip injections for the entire 7 day experiment. All mice will be checked for survival and weighed daily. On day 7 dpi all surviving mice will undergo a 6-hour morning fast with water allowed, have their blood glucose level and weight determined, be sacrificed, and relative survival, weights and blood glucose levels determined.

At 7 dpi we predict to observe near 100% lethality in Group 1 (Placebo), some improvements in survival in Group 2 (HCT), but significantly increased survival in Group 3 (CAR+HCT) mice relative to both Groups 1 & 2. We would also expect to observe amelioration of weight loss in the Group 3 mice relative to Groups 1 & 2.

We would also expect to observe lower incidence of hyperglycemia and lower blood glucose levels in Group 3 relative to Group 2.

B. Multicenter, Open-Label Study to Evaluate the Effect of CAR Co-Administration with Steroids.

Following confirmatory proof of concept demonstration data in mouse models of COVID as described in A. above, and successful IND-enabling toxicology and safety pharmacology testing of CAR peptide, the following clinical trials will be conducted:

The study will be a multicenter, open-label study to evaluate the effect of CAR co-administration with Dexamethasone (Dex) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 15:
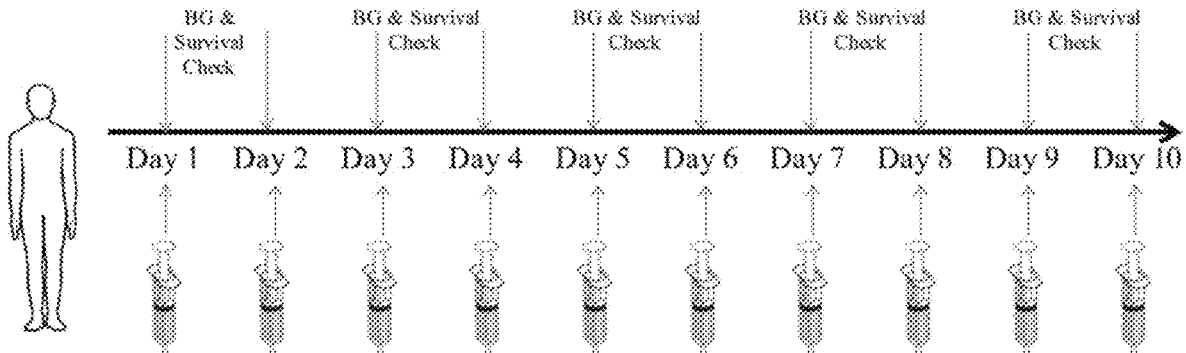
FIG. 15 shows a multicenter, open-label study design to evaluate the effect of CAR co-administration with dexamethasone (Dex) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (Dex)—will receive SOC plus one injection of Dexamethasone 6 mg/dose/day; Group 3 (CAR+Dex) will receive SOC plus one iv injection of Dexamethasone 6 mg/dose/day co-administered with CAR peptide administered iv 3 mg/kg.

Participants will be randomly assigned to one of three treatment groups of equal size:

Group 1 (Placebo)—will receive the current standard of care (SOC) for COVID-19 patients
Group 2 (Dex)—will receive SOC plus one injection of Dexamethasone 6 mg/dose/day
Group 3 (CAR+Dex) will receive SOC plus one iv injection of Dexamethasone 6 mg/dose/day co-administered with CAR peptide administered iv 3 mg/kg (FIG. 15).

Patients will be administered the above doses for 10 days, and we will observe patients in all groups for 30 days and note the two week and month lethality of each group and generate Kaplan-Meier survival curves. We expect the survival to be slightly higher in Group 2 (Dex) than Group 1 (Placebo) and significantly higher in Group 3 (CAR+Dex) than Groups 1 and 2. We also expect there to be better blood sugar control and reduced hyperglycemia in Group 3 relative to Group 2.

Another study will be a multicenter, open-label study to evaluate the effect of CAR co-administration with low dose Dexamethasone (Dex) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 16:
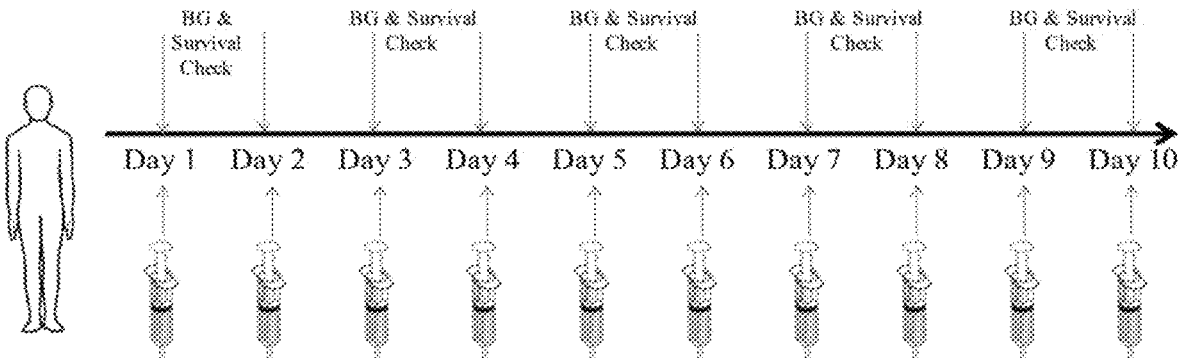
FIG. 16 shows a multicenter, open-label study design to evaluate the effect of CAR co-administration with low dose dexamethasone (Dex) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (Dex)—will receive SOC plus one injection of Dexamethasone 6 mg/dose/day; Group 3 (CAR+Low Dose Dex) will receive SOC plus one iv injection of Dexamethasone 1 mg/dose/day co-administered with CAR peptide administered iv 3 mg/kg.

Participants will be randomly assigned to one of three treatment groups of equal size:

Group 1 (Placebo)—will receive the current standard of care (SOC) for COVID-19 patients Group 2 (Dex)—will receive SOC plus one injection of Dexamethasone 6 mg/dose/day Group 3 (CAR+Low Dose Dex) will receive SOC plus one iv injection of Dexamethasone 1 mg/dose/day co-administered with CAR peptide administered iv 3 mg/kg (FIG. 16).

Patients will be administered the above doses for 10 days, and we will observe patients in all groups for 30 days and note the two week and month lethality of each group and generate Kaplan-Meier survival curves. We expect the survival to be slightly higher in Group 2 (Dex) than Group 1 (Placebo) and significantly higher in Group 3 (CAR+Low Dose Dex) than Groups 1 and 2. We also expect there to be better blood sugar control and reduced hyperglycemia in Group 3 relative to Group 2.

Another study will be a multicenter, open-label study to evaluate the effect of CAR co-administration with methyl-prednisolone (VIPS) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 17:
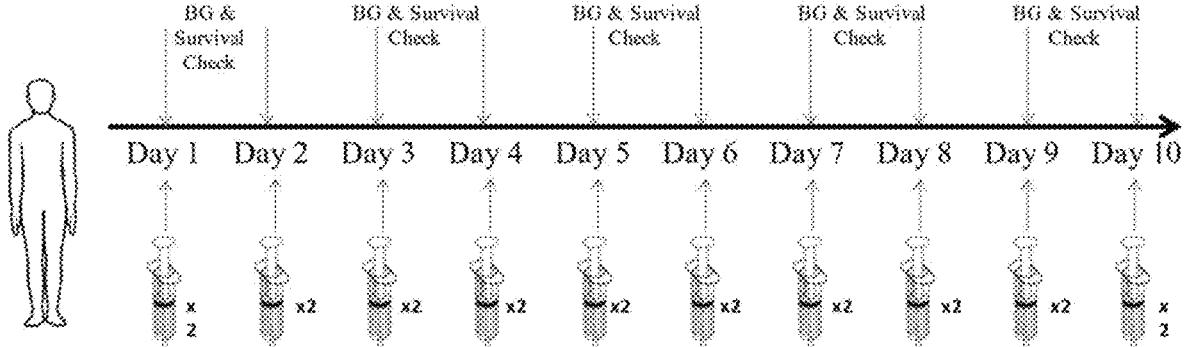
FIG. 17 shows a multicenter, open-label study design to evaluate the effect of CAR co-administration with methylprednisolone (VIPS) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (MPS)—will receive SOC plus methylprednisolone 16 mg/dose iv or oral every 12 hours for a total of 32 mg/day; Group 3 (CAR+MPS) will receive SOC plus methylprednisolone 16 mg/dose iv or oral every 12 hours for a total of 32 mg/day co-administered with CAR peptide administered iv 3 mg/kg every time MPS is given.

Participants will be randomly assigned to one of three treatment groups of equal size:

Group 1 (Placebo)—will receive the current standard of care (SOC) for COVID-19 patients Group 2 (MPS)—will receive SOC plus methylpredniso-lone 16 mg/dose iv or oral every 12 hours for a total of 32 mg/day Group 3 (CAR+MPS) will receive SOC plus methylpred-nisolone 16 mg/dose iv or oral every 12 hours for a total of 32 mg/day co-administered with CAR peptide administered iv 3 mg/kg every time MPS is given (FIG. 17).

Patients will be administered the above doses for 10 days, and we will observe patients in all groups for 30 days and note the two week and month lethality of each group and generate Kaplan-Meier survival curves. We expect the survival to be slightly higher in Group 2 (MPS) than Group 1 (Placebo) and significantly higher in Group 3 (CAR+MPS) than Groups 1 and 2. We also expect there to be better blood sugar control and reduced hyperglycemia in Group 3 relative to Group 2.

Another study will be a multicenter, open-label study to evaluate the effect of CAR co-administration with low dose methylprednisolone (MPS) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 18:
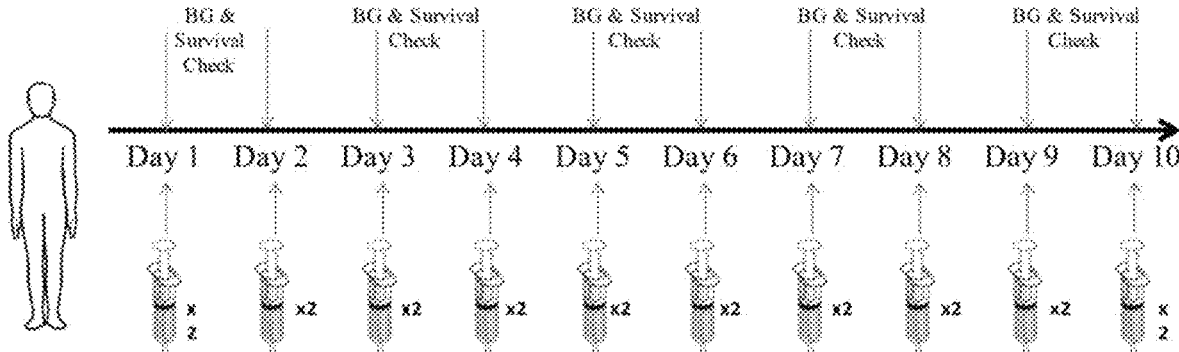
FIG. 18 shows a multicenter, open-label study design to evaluate the effect of CAR co-administration with low dose methylprednisolone (MPS) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (MPS)—will receive SOC plus methylprednisolone 16 mg/dose iv or oral every 12 hours for a total of 32 mg/day; Group 3 (CAR+Low Dose MPS) will receive SOC plus methylprednisolone 2 mg/dose iv or oral every 12 hours for a total of 4 mg/day co-administered with CAR peptide administered iv 3 mg/kg every time MPS is given.

Participants will be randomly assigned to one of three treatment groups of equal size:

Group 1 (Placebo)—will receive the current standard of care (SOC) for COVID-19 patients Group 2 (MPS)—will receive SOC plus methylpredniso-lone 16 mg/dose iv or oral every 12 hours for a total of 32 mg/day Group 3 (CAR+Low Dose MPS) will receive SOC plus methylprednisolone 2 mg/dose iv or oral every 12 hours for a total of 4 mg/day co-administered with CAR peptide administered iv 3 mg/kg every time MPS is given (FIG. 18).

Patients will be administered the above doses for 10 days, and we will observe patients in all groups for 30 days and note the two week and month lethality of each group and generate Kaplan-Meier survival curves. We expect the survival to be slightly higher in Group 2 (Low Dose MPS) than Group 1 (Placebo) and significantly higher in Group 3 (CAR+Low Dose MPS) than Groups 1 and 2. We also expect there to be better blood sugar control and reduced hyperglycemia in Group 3 relative to Group 2.

Another study will be a multicenter, open-label study to evaluate the effect of CAR co-administration with hydro-cortisone (HCT) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 19:
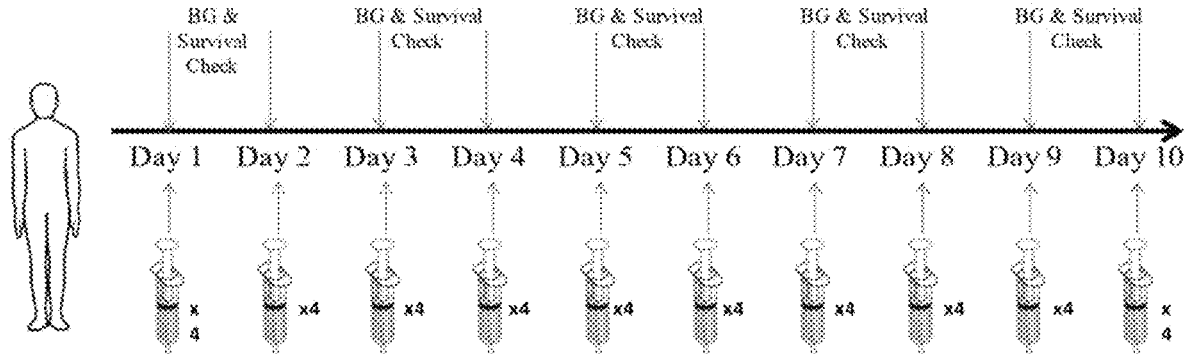
FIG. 19 shows a multicenter, open-label study design to evaluate the effect of CAR co-administration with hydrocortisone (HCT) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (HCT)—will receive SOC plus hydrocortisone 40 mg/dose iv or oral every 6 hours for a total of 160 mg/day; Group 3 (CAR+HCT) will receive SOC plus hydrocortisone 40 mg/dose iv or oral every 6 hours for a total of 160 mg/day co-administered with CAR peptide administered iv 3 mg/kg every time HCT is given.

Participants will be randomly assigned to one of three treatment groups of equal size:

Group 1 (Placebo)—will receive the current standard of care (SOC) for COVID-19 patients Group 2 (HCT)—will receive SOC plus hydrocortisone 40 mg/dose iv or oral every 6 hours for a total of 160 mg/day Group 3 (CAR+HCT) will receive SOC hydrocortisone 40 mg/dose iv or oral every 6 hours for a total of 160 mg/day co-administered with CAR peptide administered iv 3 mg/kg every time HCT is given (FIG. 19).

Patients will be administered the above doses for 10 days, and we will observe patients in all groups for 30 days and note the two week and month lethality of each group and generate Kaplan-Meier survival curves. We expect the survival to be slightly higher in Group 2 (HCT) than Group 1 (Placebo) and significantly higher in Group 3 (CAR+HCT) than Groups 1 and 2. We also expect there to be better blood sugar control and reduced hyperglycemia in Group 3 relative to Group 2.

Another study will be a multicenter, open-label study to evaluate the effect of CAR co-administration with hydro-cortisone (HCT) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints.

Figure 20:
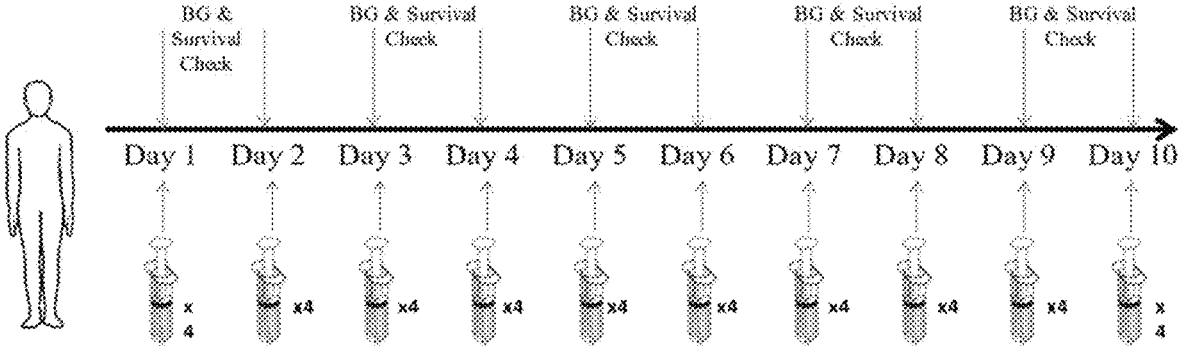
FIG. 20 shows a multicenter, open-label study design to evaluate the effect of CAR co-administration with low dose hydrocortisone (HCT) on COVID-19 mortality rate and blood sugar control. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)—will receive the current standard of care (SOC) for COVID-19 patients; Group 2 (HCT)—will receive SOC plus hydrocortisone 40 mg/dose iv or oral every 6 hours for a total of 160 mg/day; Group 3 (CAR+Low Dose HCT) will receive SOC plus hydrocortisone 8 mg/dose iv or oral every 6 hours for a total of 32 mg/day co-administered with CAR peptide administered iv 3 mg/kg every time HCT is given.

Participants will be randomly assigned to one of three treatment groups of equal size:

Group 1 (Placebo)—will receive the current standard of care (SOC) for COVID-19 patients Group 2 (HCT)—will receive SOC plus hydrocortisone 40 mg/dose iv or oral every 6 hours for a total of 160 mg/day Group 3 (CAR+Low Dose HCT) will receive SOC hydro-cortisone 8 mg/dose iv or oral every 6 hours for a total of 32 mg/day co-administered with CAR peptide administered iv 3 mg/kg every time low dose HCT is given (FIG. 20).

Patients will be administered the above doses for 10 days, and we will observe patients in all groups for 30 days and note the two week and month lethality of each group and generate Kaplan-Meier survival curves. We expect the survival to be slightly higher in Group 2 (Low Dose HCT) than Group 1 (Placebo) and significantly higher in Group 3 (CAR+Low Dose HCT) than Groups 1 and 2. We also expect there to be better blood sugar control and reduced hyperglycemia in Group 3 relative to Group 2.

C. CAR+Antivirals for COVID Animals and Human Result-ing in Improved Survival.

In a proof-of-concept experiment, we will use the K18-hACE2 transgenic mouse model (Jackson Lab #034860)

which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3\times10^4$ plaque-forming units. The lethality of the disease model can be modified by altering the volume of virus titer administered to the K18-hACE2 mice, with the 50% lethal dose of SARS-CoV for K18-hACE2 mice was less than 230 plaque-forming unit after intranasal inoculation. SARS-Cov2 infected K18-hACE2 mice also suffer rapid weight loss with lethargy and labored breathing.

In an initial experiment to demonstrate the utility of CAR peptide for treating COVID-19 disease in humans, we will take 60 K18-hACE2 male transgenic mice (Jackson Lab #034860) and administer intranasal inoculations of SARS-CoV2 at $2.3\times10^4$ plaque-forming units to each mouse and divide them into 3 equal-sized treatment groups of 20 mice each:

Group 1 (Placebo)—will receive placebo (PBS) injections ip every 12 hours

Group 2 (RDV)—will receive remdesivir 25 mg/kg/dose ip every 12 hours

Figure 21:
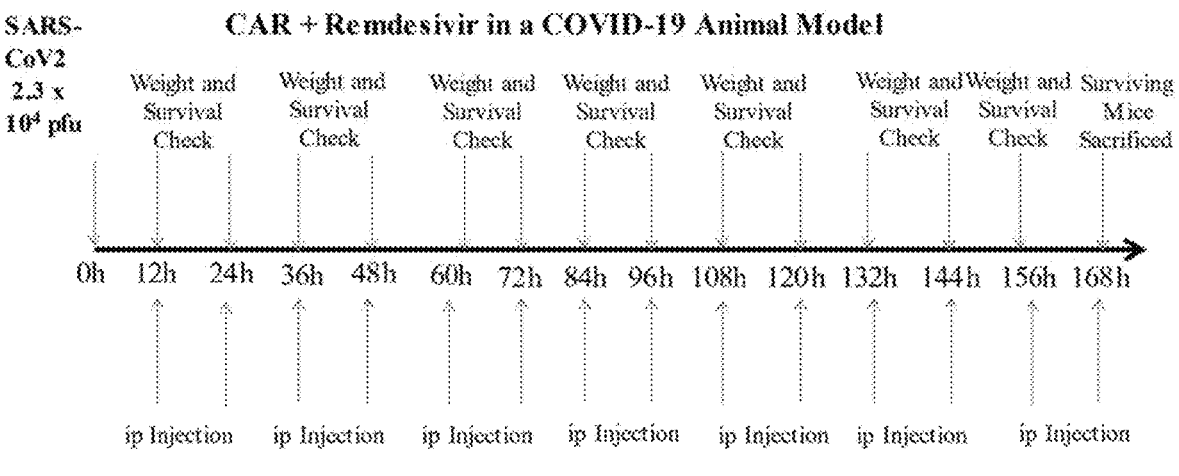
FIG. 21 shows a proof-of-concept experiment, using the K18-hACE2 transgenic mouse model, which has been modified to incorporate human angiotensin I-converting enzyme 2 (hACE2). 60 K18-hACE2 male transgenic mice are used, with administration of intranasal inoculations of SARS-CoV2 at $2.3 \times 10^4$ plaque-forming units to each mouse, then dividing them into 3 equal-sized treatment groups of 20 mice each: Group 1 (Placebo)—will receive placebo (PBS) injections ip every 12 hours; Group 2 (RDV)—will receive remdesivir 25 mg/kg/dose ip every 12 hours; Group 3 (CAR+RDV)—will receive remdesivir 25 mg/kg/dose ip every 12 hours co-administered with CAR peptide administered ip 8 mg/kg every 12 hours.
Figure 21:

Group 3 (CAR+RDV)—will receive remdesivir 25 mg/kg/dose ip every 12 hours co-administered with CAR peptide administered ip 8 mg/kg every 12 hours (FIG. 21).

We will inoculate mice on Day 0 dpi, and initiate the respective treatments on day 1 dpi and continue with twice daily ip injections for the entire 7-day experiment. All mice will be weighed daily, and checked for survival twice daily. On day 7 dpi all surviving mice will be sacrificed, and relative survival determined.

At 7 dpi we predict to observe near 100% lethality in Group 1 (Placebo), some improvements in survival in Group 2 (RDV), but significantly increased survival in Group 3 (CAR+RDV) mice relative to both Groups 1 & 2. We would also expect to observe amelioration of weight loss in the Group 3 mice relative to Groups 1 & 2

Following confirmatory proof-of-concept demonstration data in mouse models of COVID as described in C. above, and successful IND-enabling toxicology and safety pharmacology testing of CAR peptide, the following clinical trial will be conducted:

The study will be a multicenter, open-label study to evaluate the effect of CAR co-administration with remdesivir (RDV) on COVID-19 mortality rate. Eligible patients will be hospitalized patients requiring oxygen support that have confirmed SARS-CoV-2 infection. Two-week (14 day) and one month (30 day) lethality rates are the co-primary endpoints.

Figure 22:
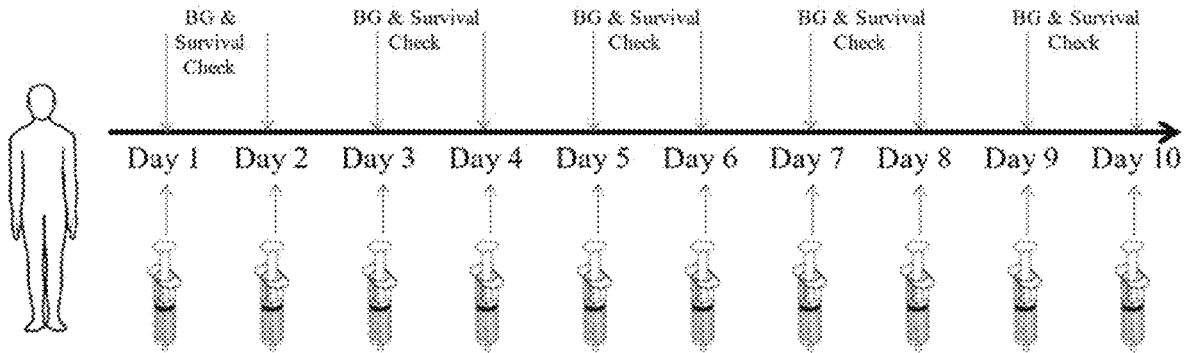
FIG. 22 shows a multicenter, open-label study design to evaluate the effect of CAR co-administration with remdesivir (RDV) on COVID-19 mortality rate. Eligible patients will be hospitalized patients requiring oxygen support that have confirmed SARS-CoV-2 infection. Two-week (14 day) and one month (30 day) lethality rates are the co-primary endpoints. Participants will be randomly assigned to one of three treatment groups of equal size: Group 1 (Placebo)— will receive the current standard of care (SOC) for COVID-19 patients; Group 2 (RDV)—will receive SOC plus one injection of remdesivir 200 mg day 1, 100 mg/day days 2-10, infused iv over 30-120 min; Group 3 (CAR+RDV) will receive SOC plus remdesivir dosed at 200 mg day 1, 100 mg/day days 2-10 co-administered with CAR peptide 3 mg/kg. infused iv over 30-120 min every day.

Participants will be randomly assigned to one of three treatment groups of equal size:

Group 1 (Placebo)—will receive the current standard of care (SOC) for COVID-19 patients Group 2 (RDV)—will receive SOC plus one injection of remdesivir 200 mg day 1, 100 mg/day days 2-10, infused iv over 30-120 min Group 3 (CAR+RDV) will receive SOC plus remdesivir dosed at 200 mg day 1, 100 mg/day days 2-10 co-administered with CAR peptide 3 mg/kg. infused iv over 30-120 min every day (FIG. 22).

Patients will be administered the above doses for 10 days, and patients will be observed in all groups for 30 days and note the two week and month lethality of each group and generate Kaplan-Meier survival curves. We expect the survival to be slightly higher in Group 2 (RDV) than Group 1 (Placebo) and significantly higher in Group 3 (CAR+RDV) than Groups 1 and 2.

D. CAR+Anticoagulants for COVID Animals and Humans Resulting in Improved Survival.

In a proof-of-concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3\times10^4$ plaque-forming units. The lethality of the disease model can be modified by altering the volume of virus titer administered to the K18-hACE2 mice, with the 50% lethal dose of SARS-CoV2 for K18-hACE2 mice was less than 230 plaque-forming unit after intranasal inoculation. SARS-Cov2 infected K18-hACE2 mice also suffer rapid weight loss with lethargy and labored breathing.

In an initial experiment to demonstrate the utility of CAR peptide for treating COVID-19 disease in humans, we will take 60 K18-hACE2 male transgenic mice (Jackson Lab #034860) and administer intranasal inoculations of SARS-CoV2 at $2.3\times10^4$ plaque-forming units to each mouse and divide them into 3 equal-sized treatment groups of 20 mice each:

Group 1 (Placebo)—will receive placebo (PBS) injections ip every 12 hours

Group 2 (ATIII)—will receive antithrombin III 300IU/kg/dose ip every 24 hours

Group 3 (CAR+ATIII)—will receive antithrombin III 300IU/kg/dose ip every 24 hours co-administered with CAR peptide administered ip 8 mg/kg every 24 hours (FIG. 23).

Agatroban for humans: 0.7 mg/kg/day infused at a rate of 1 ug/kg/min for a total dose of 50 mg for a 71.4 kg human. Activate partial thromboplastin time (aPTT) must be monitored to maintain a range of 30-40 seconds. If aPTT remains too high, administer supplemental doses of agrobatan, if aPTT is too low, reduce agratrabon dose. +/−CAR 3 mg/kg co-infusion at a rate of 5 ug/kg/min (FIG. 24).

E. CAR+Steroids+Antivirals for Animals and Humans Resulting in Improved Survival.

In a proof-of-concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3\times10^4$ plaque-forming units. The lethality of the disease model can be modified by altering the volume of virus titer administered to the K18-hACE2 mice, with the 50% lethal dose of SARS-CoV2 for K18-hACE2 mice was less than 230 plaque-forming unit after intranasal inoculation. SARS-Cov2 infected K18-hACE2 mice also suffer rapid weight loss with lethargy and labored breathing.

In an initial experiment to demonstrate the utility of CAR peptide for treating COVID-19 disease in humans, we will take 60 K18-hACE2 male transgenic mice (Jackson Lab #034860) and administer intranasal inoculations of SARS-CoV2 at $2.3\times10^4$ plaque-forming units to each mouse and divide them into 3 equal-sized treatment groups of 20 mice each:

Group 1 (Placebo)—will receive placebo (PBS) injections ip every 12 hours

Group 2 (RDV+Dex)—will receive remdesivir 25 mg/kg/dose ip every 12 hours and dexamethasone 0.15 mg/kg/dose ip every 24 hours Group 3 (CAR+RDV+Dex)—will receive remdesivir 25 mg/kg/dose ip every 12 hours co-administered with CAR peptide administered ip 8 mg/kg every 12 hours and dexamethasone 0.15 mg/kg/dose ip every 24 hours (FIG. 25).

We will inoculate mice on Day 0 dpi, and initiate the respective treatments on day 1 dpi and continue with twice daily ip injections for the entire 7-day experiment. All mice will be weighed daily. On day 7 dpi all surviving mice with be sacrificed, and relative survival determined.

At 7 dpi we predict to observe near 100% lethality in Group 1 (Placebo), some improvements in survival in Group 2 (RDV+Dex), but significantly increased survival in Group 3 (CAR+RDV+Dex) mice relative to both Groups 1 & 2. We would also expect to observe amelioration of weight loss in the Group 3 mice relative to Groups 1 & 2.

We would also expect to observe lower incidence of hyperglycemia in Group 3 relative to Group 2.

F. CAR+Antibodies for COVID Animals and Humans Resulting in Improved Survival.

Following confirmatory proof-of-concept demonstration data in mouse models of COVID as described in E. above, and successful IND-enabling toxicology and safety pharmacology testing of CAR peptide, the following clinical trial will be conducted:

The study will be a multicenter, open-label study to evaluate the effect of CAR co-administration with tocilizumab (TOC) on COVID-19 mortality rate. Eligible patients will be hospitalized patients that have confirmed SARS-CoV-2 infection. Two-week (14 day) and one month (30 day) lethality rates are the co-primary endpoints.

Participants will be randomly assigned to one of three treatment groups of equal size:

Group 1 (Placebo)—will receive the current standard of care (SOC) for COVID-19 patients Group 2 (TOC)—will receive one injection of tocilizumab 8 mg/kg Group 3 (CAR+TOC)—will receive one injection of tocilizumab 8 mg/kg co-administered with CAR peptide administered ip 3 mg/kg.

We will observe patients in all groups for 30 days and note the two week and month lethality of each group. We expect the lethality to be slightly higher in Group 2 (TOC) than Group 1 (Placebo) and significantly higher in Group 3 (CAR+TOC) than Groups 1 and 2.

G. CAR+Steroids+Antivirals+Antibodies for Animals and Humans Resulting in Improved Survival.

Following confirmatory proof-of-concept demonstration data in mouse models of COVID as described in F. above, and successful IND-enabling toxicology and safety pharmacology testing of CAR peptide, the following clinical trial will be conducted:

The study will be a multicenter, open-label study to evaluate the effect of CAR co-administration with tocilizumab (TOC) on COVID-19 mortality rate. Eligible patients will be hospitalized patients that have confirmed SARS-CoV2 infection. Two-week (14 day) and one month (30 day) lethality rates are the co-primary endpoints.

Participants will be randomly assigned to one of three treatment groups of equal size:

Group 1 (Placebo)—will receive the current standard of care (SOC) for COVID-19 patients.

Group 2 (TOC+RDV+Dex)—will receive one injection of tocilizumab 8 mg/kg, remdesivir 25 mg/kg/dose ip every 12 hours and dexamethasone 0.15 mg/kg/dose ip every 24 hours.

Group 3 (CAR+TOC+RDV+Dex)—will receive one injection of tocilizumab 8 mg/kg remdesivir 25 mg/kg/dose ip every 12 hours and dexamethasone 0.15 mg/kg/dose ip every 24 hours co-administered with CAR peptide administered ip 3 mg/kg.

We will observe patients in all groups for 30 days and note the two week and month lethality of each group. We expect the lethality to be slightly higher in Group 2 (TOC) than Group 1 (Placebo) and significantly higher in Group 3 (CAR+TOC) than Groups 1 and 2.

We would also expect to observe lower incidence of hyperglycemia in Group 3 relative to Group 2.

H. CAR+Interferon for COVID Animals and Humans Resulting in Improved Survival.

We will use the K18-hACE2 transgenic mouse model that has been modified to incorporate human angiotensin I-converting enzyme 2 (hACE2) and are susceptible to SARS—CoV2 infection. To demonstrate the effectiveness of CAR in treating COVID, we will take 60 K18-hACE2 male transgenic mice (Jackson Lab #034860) and administer intranasal inoculations of SARS-CoV2 at $2.3 \times 10^4$ plaque-forming units to each mouse and divide them into 3 equal-sized treatment groups of 20 mice each:

Group 1 (Placebo)—will receive placebo (PBS) injections i.p.

Group 2 (interferon)—will receive interferon (2 µg)

Group 3 (CAR+interferon)—will receive interferon (2 µg) co-administered with CAR peptide (3 mg/kg) (FIG. 26).

We will inoculate mice on Day 0 dpi, and initiate the respective treatments on day 2 dpi and continue with daily ip injections for the entire 7-day experiment. All mice will be weighed daily. On day 7 dpi all surviving mice with be sacrificed, and relative survival determined.

At 7 dpi we predict to observe near 100% lethality in Group 1 (Placebo), some improvements in survival in Group 2 (interferon), but significantly increased survival in Group 3 (CAR+interferon) mice relative to both Groups 1 & 2. We would also expect to observe amelioration of weight loss in the Group 3 mice relative to Groups 1 & 2.

We would also expect to observe lower incidence of hyperglycemia in Group 3 relative to Group 2.

I. CAR-Nanoparticles for MRI Imaging of COVID-Inflamed Tissues.

We will use the K18-hACE2 transgenic mouse model that has been modified to incorporate human angiotensin I-converting enzyme 2 (hACE2) and are susceptible to SARS—CoV2 infection. To demonstrate the effectiveness of CAR in treating COVID, we will take 40 K18-hACE2 male transgenic mice (Jackson Lab #034860) and administer intranasal inoculations of SARS-CoV2 at $2.3 \times 10^4$ plaque-forming units to each mouse and divide them into 2 equal-sized treatment groups of 20 mice each:

Group 1 (GAD) gadobutrol

Group 2 (CAR-Fe$_2$O$_3$NPs)—will receive CAR-Fe$_2$O$_3$NPs (CAR peptide—iron oxide nanoparticle contrast agent at a concentration of 100 µg/ml (FIG. 27).

The animals received one intravenous standard dose of 0.1 mmol/kg body weight of each contrast agent by bolus administration, using a power injector via a peripheral vein. To ensure that the injection duration was comparable, 1.0 M gadobutrol was administered at a rate of 1.5 to 2 mL/s and 0.5 M gadopentetate dimeglumine was administered at a rate of 2 to 3 mL/s. Administrations were followed by a 10 mL 0.9% saline flush at the same rate as the contrast agent We expect to observe that the Group 2 (CAR-Fe$_2$O$_3$NPs) contrast agent will better enable the determination and visualization of the presence, extent and degree of COVID inflammation and damage across multiple tissues and organs affected by SARS—CoV2 infection than Group 1 contrast agent.

In order to observe the effects of the CAR peptide on imaging using an alternative compound, we will set up 2 additional groups:

Group 1 (GDP) gadopentetate dimeglumine

Group 2 (CAR-Fe$_2$O$_3$NPs)—will receive CAR-Fe$_2$O$_3$NPs (CAR peptide—iron oxide nanoparticle contrast agent at a concentration of 100 μg/ml (FIG. 28).

The patients received one intravenous standard dose of 0.1 mmol/kg body weight of each contrast agent by bolus administration, using a power injector via a peripheral vein. To ensure that the injection duration was comparable, 1.0 M gadobutrol was administered at a rate of 1.5 to 2 mL/s and 0.5 M gadopentetate dimeglumine was administered at a rate of 2 to 3 mL/s. Administrations were followed by a 10 mL 0.9% saline flush at the same rate as the contrast agent We expect to observe that Group 2 (CAR—Fe$_2$O$_3$NPs) contrast agent will better enable the determination and visualization of the presence, extent and degree of COVID inflammation and damage across multiple tissues and organs affected by SARS—CoV2 infection than Group 1 contrast agent.

This yielded enhanced imaging results in COVID-inflamed tissues relative to Group 1 (Scrambled CAR+NP) & 2 (NP alone).

J. CAR-Chelate for PET Scanning of COVID-Inflamed Tissues.

In a proof concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at 2.3×10$^4$ plaque-forming units. The lethality of the disease model can be modified by altering the volume of virus titer administered to the K18-hACE2 mice, with the 50% lethal dose of SARSCoV2 for K18-hACE2 mice was less than 230 plaque-forming unit after intranasal inoculation. SARS-Cov2 infected K18-hACE2 mice also suffer rapid weight loss with lethargy and labored breathing.

First, $^{64}$Cu-DOTA-CAR and $^{64}$Cu-DOTA must be validated. DOTA-CAR will be prepared by conjugating DOTA to a cysteine residue of CAR. The DOTA-CAR conjugate will be radiolabeled with $^{64}$CuCl$_2$, resulting in $^{64}$Cu-DOTA-CAR and tested for stability.

In an experiment to demonstrate the utility of CAR-chelate for PET/CT scanning of COVID-19-inflamed tissues in humans, we will take 30 K18-hACE2 male transgenic mice (Jackson Lab #034860) and administer intranasal inoculations of SARS-CoV2 at 2.3×10$^4$ plaque-forming units to each mouse. Once the mice have developed into an appropriate model for SARS-CoV-2, and divide them into 2 groups of 15 SARSCoV2-infected K18-hACE2 mice each:

Group 1 ($^{64}$Cu-DOTA): SARS-CoV2-infected K18-hACE2 mice will receive 100 μL of $^{64}$CuDOTA via the tail vein;

Group 2 (64Cu-DOTA-CAR): SARS-CoV2-infected K18-hACE2 mice will receive 100 μL of $^{64}$Cu-DOTA-CAR via the tail vein (FIG. 29).

To compare the uptake of CAR-chelate in an infected mouse to that of control mouse, we will take 30 C57BL/6J male mice (Jackson Lab #000664) and administer PBS to each mouse and divide them into 2 groups of 15 mice each:

Group 3 (control mouse+$^{64}$Cu-DOTA): will receive 100 μL of $^{64}$Cu-DOTA via the tail vein;

Group 4 (control mouse+$^{64}$Cu-DOTA-CAR): will receive 100 μL $^{64}$CuDOTA-CAR.

Assessment of $^{64}$Cu-DOTA-CAR uptake and $^{64}$Cu-DOTA by tissues 1 hour after injection: After 1 hour of injection with CAR-chelate or chelate alone, the concentration of tracer will be calculated. We expect to observe the highest uptake concentration of $^{64}$Cu-DOTA-CAR injected organs of infected mice, followed by $^{64}$Cu-DOTA injected organs of infected mice, then similar concentrations of $^{64}$Cu-DOTA and $^{64}$Cu-DOTA-CAR injected organs in control mice.

Assessment of PET Imaging: After 1 hour of injection in infected mice, we expect increased intensity to be observed in the pulmonary artery of mice injected with $^{64}$Cu-DOTA-CAR in comparison to the pulmonary artery of mice injected with $^{64}$Cu-DOTA. We expect to see reduced of signals in both groups of control mice, which will show similar intensities in pulmonary arteries. (Group 3 and Group 4).

K. CAR-Au for CT Scan of COVID-Inflamed Tissues.

In a proof concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at 2.3×10$^4$ plaque-forming units. The lethality of the disease model can be modified by altering the volume of virus titer administered to the K18-hACE2 mice, with the 50% lethal dose of SARS-CoV2 for K18-hACE2 mice was less than 230 plaque-forming unit after intranasal inoculation. SARS-CoV2 infected K18-hACE2 mice also suffer rapid weight loss with lethargy and labored breathing.

CAR-Au is validated as follows:

In an experiment to demonstrate the utility of CAR-Au for CT scan of COVID19-inflamed tissues in humans, we will take 30 K18-hACE2 male transgenic mice (Jackson Lab #034860) and administer intranasal inoculations of SARS-CoV2 at 2.3×10$^4$ plaque-forming units to each mouse. Once the mice have developed into an appropriate model for SARS-CoV2, and divide them into 2 groups of 15 mice each:

Group 1 (Au nps): each mouse will receive an IV administration of 0.1 mL of 1.33 nM Au nps, 8×1011 nps/mL via tail vein.

Group 2 (CAR-Au nps): each mouse will receive an IV administration of 0.1 mL of 1.33 nM CAR-Au nps, 8×1011 nps/mL via tail vein (FIG. 30).

Assessment Au and CAR-Au uptake 1 hour after injection: After 1 hour of injection Au alone or CAR-Au, the concentration of tracer will be calculated. We expect to observe the highest concentration of tracer in the lungs of SARSCoV2-infected K18-hACE2 mice injected with Group 1 (CAR-Au) relative to Group 2 (Au).

Assessment of CT Imaging: After 1 hour of injection in SARS-CoV2-infected K18-hACE2 mice, we expect increased intensity to be observed in the lungs of SARS-CoV2-infected K18-hACE2 mice injected with Group 1 (CAR-Au) in comparison to the Group 2 (Au only).

Validation for Human Use:

In an experiment to demonstrate the utility of CAR-Au for CT scan of COVID-19 inflamed tissues in humans, we will compare the efficacy of current iodine contrast agents vs CAR-Au nanoparticles.

Group 1 (IOD): each patient will receive an IV administration of 80 mL of iohexol (OMNIPAQUE 350) at a rate of 7.5 mL/second to 30 mL/second using a pressure injector.

Group 2 (CAR-Au nps): each patient will receive an IV administration of 80 mL of 1.33 nM CAR-Au nps, 8×1011 nps/mL at a rate of 7.5 mL/second to 30 mL/second using a pressure injector.

Assessment Au and CAR-Au uptake 1 hour after injection: After 1 hour of injection of Iodine or CAR-Au, the concentration of tracer will be calculated. We expect to observe the highest concentration of tracer in the lungs of COVID-19 patients injected with Group 1 (CAR-Au) relative to Group 2 (IOD).

Assessment of CT Imaging: After 1 hour of injection of iodine or CAR-Au contrast agents, we expect increased intensity to be observed in the lungs of COVID-19 patients injected with Group 1 (CAR-Au) relative to Group 2 (IOD).

L. CAR-Liposomes Containing Steroids for Inhaled Relief of COVID Lung Injury.

In a proof of concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3\times10^4$ plaque-forming units. The lethality of the disease model can be modified by altering the volume of virus titer administered to the K18-hACE2 mice, with the 50% lethal dose of SARS-CoV2 for K18-hACE2 mice was less than 230 plaque-forming unit after intranasal inoculation. SARS-Cov2 infected K18-hACE2 mice also suffer rapid weight loss with lethargy and labored breathing.

In an experiment to demonstrate the utility of CAR-liposomes peptide for treating COVID-19 disease in humans, we will take 80 K18-hACE2 male transgenic mice (Jackson Lab #034860) and administer intranasal inoculations of SARS-CoV2 at $2.3\times10^4$ plaque-forming units to each mouse. Once the mice have developed into an appropriate model for SARS-CoV2, and divide them into 2 studies of equal size: pulmonary retention and survival.

First, liposomes must be formulated using a previously validated method and characterized for size, polydispersity index (PDI), zeta potential, and entrapment efficiency. Aerosolization stability was also determined by measuring size, PDI, zeta potential, and entrapment efficiency before and after aerosolization of the formulations. After formulating and characterizing the liposomes, studies for survival and pulmonary retention will be enacted.

For the studies measuring survival against CAR-Liposomes with antivirals, 40 mice will be broken up into 4 groups equally:

Group 1 (Placebo)—will receive PBS injected ip every 24 hours.

Group 2 (Dex)—will receive dexamethasone 0.15 mg/kg/dose via IT installation every 24 hours.

Group 3 (Dex Lip)—will receive liposome encapsulated dexamethasone 0.15 mg/kg/dose via IT installation every 24 hours.

Group 4 (CAR-Lip+Dex)—will receive CAR-liposome encapsulated dexamethasone 0.15 mg/kg/dose IT every 24 hours (FIG. 31).

We will inoculate mice on Day 0 dpi, and initiate the respective treatments on day 2 dpi and continue with daily ip injections for the entire 7-day experiment. All mice will be weighed daily. On day 7 dpi all surviving mice with be sacrificed, and relative survival determined.

At 7 dpi we predict to observe near 100% lethality in Group 1 (Placebo), some improvements in survival in Group 2 (Dex) and Group 3 (Dex Lip), but significantly increased survival in Group 4 (CAR+Dex) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Groups 2 & 3.

To demonstrate enhanced pulmonary retention of dexamethasone in CAR-liposomes versus alone or in no-CAR-liposomes, SARS—CoV2 infected K18-hACE2 mice will be studied using an IPRL system. Mouse lungs will be surgically removed from both control and SARS-CoV2 infected mice. To prepare the lungs for the determination of pulmonary retention, 200 IU/Kg heparin will be administered into the right ventricle to prevent blood clotting. A cannula will be inserted into the pulmonary artery via a small incision in the trunk of the right ventricle and another cannula into the left atrium. Next, the lungs will be perfused with a physiological lung solution made of $CaCl_2$, NaCl, KCl, $MgSO_4$, $NaH_2 PO_4$, glucose, $NaHCO_3$, and Ficoll® at pH 7.4 and 37° C. and passed a mixture of 95% 02:5% $CO_2$ gas into the medium in the reservoir. Subsequently, the lungs will be placed in a humid artificial thoracic chamber under the negative pressure at 37° C. To prevent deflation of the lungs, a negative pressure will be maintained within the thoracic chamber, letting the lungs stabilized in the artificial thoracic chamber after 5 min of perfusion. The tidal volume and ventilation frequency will be recorded and the media will be allowed to perfuse at 3-9 mL, 60 cycles/min and 10 mL/min, respectively.

CAR-liposomes encapsulated dexamethasone, no-CAR-liposome encapsulated dexamethasone, and free dexamethasone will be administered to lungs via the tracheal cannula.

Lungs will be then perfused with aforementioned perfusion media and aliquots of the perfusate will be periodically collected for 2 h and then replaced with equivalent amount of fresh perfusate.

Lungs will be stored at −80° C. for analysis. To extract the drug from the lungs, the lungs will be homogenized, centrifuged, collected the supernatant, and drug will be separated from the supernatant by methanol precipitation (5:1 v/v) followed by centrifugation at 13 300 g for 15 min and determined the drug using a previously-validated liquid chromatography-tandem mass spectrometry (LC-MS/MS) method and finally normalized the drug content to protein content of the tissue using a bicinchoninic acid assay (BCA). For all treatment groups, we determined the amount of dexamethasone in the IPRL circuitry by subtracting the amount of dexamethasone in the perfusate and lung homogenates from the dose of dexamethasone administered.

We expect that CAR-liposome encapsulated dexamethasone will yield the highest percentage of dexamethasone retained in the lungs of the mouse model.

To demonstrate CAR-liposome enhancement of methylprednisolone (MPS), SARS—CoV2 infected K18-hACE2 mice could receive methylprednisolone 2 mg/kg twice daily (every 12 hours). Liposomes will be formulated and validated as described above.

Group 1 (Placebo)—will receive PBS injected ip every 24 hours

Group 2 (MPS)—will receive MPS 2 mg/kg/dose via IT installation every 24 hours

Group 3 (MPS Lip)—will receive liposome encapsulated MPS 2 mg/kg/dose via IT installation every 24 hours Group 4 (CAR-Lip+MPS)—will receive CAR-liposome encapsulated MPS 2 mg/kg/dose IT every 24 hours (FIG. 32).

At 7 dpi we predict to observe near 100% lethality in Group 1 (Placebo), some improvements in survival in Group 2 (MPS) and Group 3 (MPS Lip), but significantly increased survival in Group 4 (CAR+MPS) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Groups 2 & 3.

To demonstrate enhanced pulmonary retention of MPS in CAR-liposomes versus alone or in no-Car-liposomes, SARS—CoV2 infected K18-hACE2 mice will be studied using an IPRL system. Mouse lungs will be surgically removed from both control and SARS-CoV2 infected mice. To prepare the lungs for the determination of pulmonary retention, 200 IU/Kg heparin will be administered into the right ventricle to prevent blood clotting. A cannula will be inserted into the pulmonary artery via a small incision in the trunk of the right ventricle and another cannula into the left atrium. Next, the lungs will be perfused with a physiological lung solution made of $CaCl_2$), NaCl, KCl, $MgSO_4$, $NaH_2PO_4$, glucose, $NaHCO_3$, and Ficoll® at pH 7.4 and 37° C. and passed a mixture of 95% 02:5% $CO_2$ gas into the medium in the reservoir. Subsequently, the lungs will be placed in a humid artificial thoracic chamber under the negative pressure at 37° C. To prevent deflation of the lungs, a negative pressure will be maintained within the thoracic chamber, letting the lungs stabilized in the artificial thoracic chamber after 5 min of perfusion. The tidal volume and ventilation frequency will be recorded and the media will be allowed to perfuse at 3-9 mL, 60 cycles/min and 10 mL/min, respectively.

CAR-liposomes encapsulated MPS, no-CAR-liposome encapsulated MPS, and free MPS will be administered to lungs via the tracheal cannula.

Lungs will be then perfused with aforementioned perfusion media and aliquots of the perfusate will be periodically collected for 2 h and then replaced with equivalent amount of fresh perfusate.

Lungs will be stored at −80° C. for analysis. To extract the drug from the lungs, the lungs will be homogenized, centrifuged, collected the supernatant, and drug will be separated from the supernatant by methanol precipitation (5:1 v/v) followed by centrifugation at 13 300 g for 15 min and determined the drug using a previously-validated liquid chromatography-tandem mass spectrometry (LC-MS/MS) method and finally normalized the drug content to protein content of the tissue using a bicinchoninic acid assay (BCA). For all treatment groups, we determined the amount of MPS in the IPRL circuitry by subtracting the amount of MPS in the perfusate and lung homogenates from the dose of MPS administered.

We expect that CAR-liposome encapsulated MPS will yield the highest percentage of MPS retained in the lungs of the mouse model.

To demonstrate CAR enhancement of hydrocortisone (HCT), SARS—Cov2 infected K18-hACE2 mice could receive hydrocortisone 0.2 mg/kg four times daily (every 6 hours). Liposomes will be formulated and validated as described above.

Group 1 (Placebo)—will receive PBS injected ip every 24 hours

Group 2 (HCT)—will receive HCT 0.2 mg/kg/dose via IT installation every 24 hours Group 3 (HCT Lip)—will receive liposome encapsulated HCT 0.2 mg/kg dose via IT installation every 24 hours Group 4 (CAR-Lip+HCT)—will receive Car-liposome encapsulated HCT 0.2 mg/kg/dose IT every 24 hours (FIG. 33).

At 7 dpi we predict to observe near 100% lethality in Group 1 (Placebo), some improvements in survival in Group 2 (HCT) and Group 3 (HCT Lip), but significantly increased survival in Group 4 (CAR+HCT) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Group 2 & 3.

M. CAR-Liposomes Containing Steroids for iv Injection for COVID Animals and Humans Resulting in Improved Survival.

In a proof concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3 \times 10^4$ plaque-forming units. The lethality of the disease model can be modified by altering the volume of virus titer administered to the K18-hACE2 mice, with the 50% lethal dose of SARS-CoV2 for K18-hACE2 mice was less than 230 plaque-forming unit after intranasal inoculation. SARS-CoV2 infected K18-hACE2 mice also suffer rapid weight loss with lethargy and labored breathing.

In an initial experiment to demonstrate the utility of CAR-liposomes for treating COVID-19 disease in humans, we will take 60 K18-hACE2 male transgenic mice (Jackson Lab #034860) and administer intranasal inoculations of SARS-CoV2 at $2.3 \times 10^4$ plaque-forming units to each mouse.

First, liposomes must be formulated using a previously validated method and characterized for size, polydispersity index (PDI), zeta potential, and entrapment efficiency. Aerosolization stability was also determined by measuring size, PDI, zeta potential, and entrapment efficiency before and after aerosolization of the formulations. After formulating and characterizing the liposomes, studies for survival and pulmonary retention will be enacted.

Mice will be divided into 4 equal-sized treatment groups of 15 mice each:

Group 1 (Placebo)—will receive saline injected iv every 24 hours

Group 2 (Dex)—will receive dexamethasone 0.15 mg/kg/dose iv every 24 hours

Group 3 (Dex Lip)—will receive liposome encapsulated dexamethasone 0.15 mg/kg/dose iv every 24 hours Group 4 (CAR-Lip+Dex)—will receive CAR-liposome encapsulated dexamethasone 0.15 mg/kg/dose iv every 24 hours (FIG. 34).

We will inoculate mice on Day 0 dpi, and initiate the respective treatments on day 2 dpi and continue with daily iv injections for the entire 7-day experiment. All mice will be weighed daily. On day 7 dpi all surviving mice with be sacrificed, and relative survival determined.

At 7 dpi we predict to observe near 100% lethality in Group 1 (Placebo), some improvements in survival in Group 2 (Dex) and Group 3 (Dex Lip), but significantly increased survival in Group 4 (CAR-Lip+Dex) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Group 3.

To demonstrate CAR-liposomes enhancement of methylprednisolone (MPS), SARS—CoV2 infected K18-hACE2 mice could receive methylprednisolone 2 mg/kg twice daily (every 12 hours). Liposomes will be formulated and validated as described above.

Group 1 (Placebo)—will receive saline iv.

Group 2 (MPS)—will receive MPS 2 mg/kg/dose iv every 12 hours

Group 3 (MPS Lip)—will receive liposome encapsulated MPS 2 mg/kg/dose iv every 12 hours Group 4 (CAR-Lip+MPS)—will receive CAR-liposome encapsulated MPS 2 mg/kg/dose iv every 12 hours (FIG. 35).

At 7 dpi we predict to observe near 100% lethality in Group 1 (Placebo), some improvements in survival in Group 2 (MPS) and Group 3 (MPS Lip), but significantly increased survival in Group 4 (CAR+MPS) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Groups 2 & 3.

To demonstrate CAR-liposome enhancement of hydrocortisone (HCT), SARS—CoV2 infected K18-hACE2 mice could receive hydrocortisone 0.2 mg/kg four times daily (every 6 hours). Liposomes will be formulated and validated as described above.

Group 1 (Placebo)—will receive saline iv.

Group 2 (HCT)—will receive HCT 0.2 mg/kg/dose iv every 12 hours

Group 2 (HCT Lip)—will receive liposome encapsulated HCT 0.2 mg/kg/dose iv every 12 hours Group 3 (CAR-Lip+HCT)—will receive CAR-liposome HCT 0.2 mg/kg/dose iv every 12 hours (FIG. 36).

At 7 dpi we predict to observe near 100% lethality in Group 1 (Placebo), some improvements in survival in Group 2 (HCT) and Group 3 (HCT Lip), but significantly increased survival in Group 4 (CAR-Lip+HCT) mice relative to both Groups 1, 2 & 3. We would also expect to observe amelioration of weight loss in the Group 4 mice relative to Groups 1, 2 & 3.

We would also expect to observe lower incidence of hyperglycemia in Group 4 relative to Groups 2 & 3.

N. CAR-Liposomes Containing Antivirals for Acute Treatment of COVID Lung Injury for Animals and Humans Resulting in Improved Survival.

In a proof concept experiment, we will use the K18-hACE2 transgenic mouse model (Jackson Lab #034860) which has been modified to incorporate human angiotensin I-converting enzyme 2 (hACE2). These humanized transgenic mice are susceptible to SARS—CoV2 infection with males experiencing 100% lethality at 7 days post infection (dpi) following intranasal inoculation of SARS-CoV2 at $2.3 \times 10^4$ plaque-forming units. The lethality of the disease model can be modified by altering the volume of virus titer administered to the K18-hACE2 mice, with the 50% lethal dose of SARS-CoV for K18-hACE2 mice was less than 230 plaque-forming unit after intranasal inoculation. SARS-Cov2 infected K18-hACE2 mice also suffer rapid weight loss with lethargy and labored breathing.

In an experiment to demonstrate the utility of CAR-liposomes peptide for treating COVID-19 disease in humans, we will take 60 K18-hACE2 male transgenic mice (Jackson Lab #034860) and administer intranasal inoculations of SARS-CoV2 at $2.3 \times 10^4$ plaque-forming units to each mouse. Once the mice have developed into an appropriate model for SARS-CoV2, and divide them into 2 studies of equal size: pulmonary retention and survival.

First, liposomes must be formulated using a previously validated method and characterized for size, polydispersity index (PDI), zeta potential, and entrapment efficiency. Aerosolization stability was also determined by measuring size, PDI, zeta potential, and entrapment efficiency before and after aerosolization of the formulations. After formulating and characterizing the liposomes, studies for survival and pulmonary retention will be enacted.

For the studies measuring survival against CAR-Liposomes with antivirals, 30 mice will be broken up into 3 groups equally:

Group 1 (Rem)—will receive remdesivir analog 25 mg/kg/dose via IT installation every 24 hours Group 2 (Rem Lip)—will receive remdesivir analog liposomes 25 mg/kg/dose via IT installation every 24 hours Group 3 (CAR-Lip+Rem)—will receive CAR-liposomes with remdesivir 25 mg/kg/dose IT every 24 hours.

We will inoculate mice on Day 0 dpi, and initiate the respective treatments on day 2 dpi and continue with daily ip injections for the entire 7-day experiment. All mice will be weighed daily. On day 7 dpi all surviving mice with be sacrificed, and relative survival determined.

At 7 dpi we predict to observe near 100% lethality in Group 1 (Placebo), some improvements in survival in Group 2 (Rem Lip), but significantly increased survival in Group 3 (CAR-Lip+Rem) mice relative to both Groups 1 & 2. We would also expect to observe amelioration of weight loss in the Group 3 mice relative to Groups 1 & 2.

We would also expect to observe lower incidence of hyperglycemia in Group 3 relative to Group 2.

To demonstrate enhanced pulmonary retention of remdesivir in CAR-liposomes versus alone or in no-CAR-liposomes, SARS—CoV2 infected K18-hACE2 mice will be studied using an IPRL system. Mouse lungs will be surgically removed from both control and SARS-CoV2 infected mice. To prepare the lungs for the determination of pulmonary retention, 200 IU/Kg heparin will be administered into the right ventricle to prevent blood clotting. A cannula will be inserted into the pulmonary artery via a small incision in the trunk of the right ventricle and another cannula into the left atrium. Next, the lungs will be perfused with a physiological lung solution made of $CaCl_2$, NaCl, KCl, $MgSO_4$, $NaH_2PO_4$, glucose, $NaHCO_3$, and Ficoll® at pH 7.4 and 37° C. and passed a mixture of 95% $O2$:5% $CO_2$ gas into the medium in the reservoir. Subsequently, the lungs will be placed in a humid artificial thoracic chamber under the negative pressure at 37° C. To prevent deflation of the lungs, a negative pressure will be maintained within the thoracic chamber, letting the lungs stabilized in the artificial thoracic chamber after 5 min of perfusion. The tidal volume and ventilation frequency will be recorded and the media will be allowed to perfuse at 3-9 mL, 60 cycles/min and 10 mL/min, respectively.

Car-liposomes encapsulated remdesivir, no-CAR-liposome encapsulated remdesivir, and free remdesivir will be administered to lungs via the tracheal cannula.

Lungs will be then perfused with aforementioned perfusion media and aliquots of the perfusate will be periodically collected for 2 h and then replaced with equivalent amount of fresh perfusate.

Lungs will be stored at −80° C. for analysis. To extract the drug from the lungs, the lungs will be homogenized, centrifuged, collected the supernatant, and drug will be separated from the supernatant by methanol precipitation (5:1 v/v) followed by centrifugation at 13 300 g for 15 min and determined the drug using a previously-validated liquid chromatography-tandem mass spectrometry (LC-MS/MS) method and finally normalized the drug content to protein content of the tissue using a bicinchoninic acid assay (BCA). For all treatment groups, we determined the amount of remdesivir in the IPRL circuitry by subtracting the amount of remdesivir in the perfusate and lung homogenates from the dose of remdesivir administered.

We expect that CAR-liposome encapsulated remdesivir will yield the highest percentage of remdesivir retained in the lungs of the mouse model.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A method of treating an individual suffering from a disease, the method comprising:
   (a) providing a targeting peptide comprising a sequence substantially identical to CAR, or a variant thereof;
   (b) providing at least one therapeutic molecule selected from the group consisting of a steroid, sivelestat, and anti-thrombin III (ATIII) which conveys a measurable therapeutic benefit to a disease selected from the group consisting of sepsis, septic shock, acute respiratory distress syndrome, pneumonitis, and secondary bacterial pneumonia;
   (c) co-administering a composition comprising a) and b) to an individual in need thereof; and
   (d) measuring a therapeutic benefit to the individual;
   wherein the disease is sepsis resulting from coronavirus infection.

2. The method of claim 1, wherein the therapeutic molecule is a steroid.

3. The method of claim 2, wherein the steroid is a corticosteroid.

4. The method of claim 3, wherein the corticosteroid is at least one selected from the group consisting of dexamethasone, methylprednisolone and hydrocortisone.

5. The method of claim 1, wherein the coronavirus is SARS-CoV2 or a variant thereof.

\* \* \* \* \*